United States Patent
Tsai et al.

(10) Patent No.: US 10,435,425 B1
(45) Date of Patent: Oct. 8, 2019

(54) ALPHA-SELECTIVE SIALYL DONOR AND ITS USES FOR PREPARATION OF SIALOSIDES

(71) Applicant: Chung Yuan Christian University, Taoyuan (TW)

(72) Inventors: Yow-Fu Tsai, Taoyuan (TW); Yu-Fa Wu, Taoyuan (TW)

(73) Assignee: Chung Yuan Christian University, Taoyuan (TW)

( * ) Notice: Subject to any disclaimer, the term of this patent is extended or adjusted under 35 U.S.C. 154(b) by 0 days.

(21) Appl. No.: 16/035,625

(22) Filed: Jul. 14, 2018

(51) Int. Cl.
| | |
|---|---|
| *C07H 1/00* | (2006.01) |
| *C07H 5/10* | (2006.01) |
| *C07H 11/00* | (2006.01) |
| *C07H 13/08* | (2006.01) |
| *C07H 13/12* | (2006.01) |
| *C07H 15/12* | (2006.01) |
| *C07H 15/203* | (2006.01) |
| *C07H 17/02* | (2006.01) |

(52) U.S. Cl.
CPC .......... *C07H 1/00* (2013.01); *C07H 5/10* (2013.01); *C07H 11/00* (2013.01); *C07H 13/08* (2013.01); *C07H 13/12* (2013.01); *C07H 15/12* (2013.01); *C07H 15/203* (2013.01); *C07H 17/02* (2013.01)

(58) Field of Classification Search
None
See application file for complete search history.

(56) References Cited

PUBLICATIONS

Journal of the American Chemical Society, 2012, vol. 134 (49), pp. 20097-20102. (Year: 2012).*
Wu et al. "Assistance of the c-7,8-picoloyl moiety for directing the glycosyl acceptors into the a☐-orientation for the glycosylation of sialyl donors", Organic Letters, Jul. 28, 2017.

* cited by examiner

*Primary Examiner* — Traviss C McIntosh, III

(57) ABSTRACT

Disclosed herein a sialyl donor and its use for the synthesis of gangliosides. The sialyl donor has the structure of,

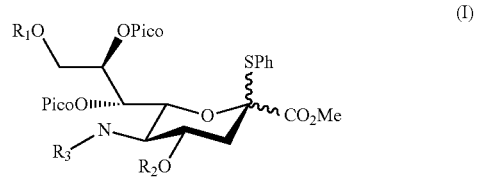

(I)

wherein, $R_1$ and $R_2$ are independently benzoyl, toluenesulfonyl, pivaloyl or acetyl optionally substituted with a halogen; and $R_3$ is acetyl or —(O)CCH$_2$OH. In one preferred embodiment, in the sialyl donor of formula (I), R is acetyl. Also disclosed herein is a method of synthesizing a sialoside. The method comprises steps of: coupling the sialyl donor of formula (I) with a glycosyl acceptor having a primary hydroxyl group in the presence of N-iodosuccinimide (NIS) and trifluoromethanesulfonic acid (TfOH) under suitable conditions; and isolating the sialoside, which has an α-glycosidic linkage. According to preferred embodiments, the coupling is conducted in a solvent selected from the group consisting of, CH$_3$CN, CH$_3$Cl, and CH$_2$Cl$_2$ at a temperature between −20° C. to −60° C. Additionally or optionally, the coupling is conducted in CH$_2$Cl$_2$ with the presence of a powdered molecular sieve at −40° C.

9 Claims, No Drawings

ALPHA-SELECTIVE SIALYL DONOR AND ITS USES FOR PREPARATION OF SIALOSIDES

STATEMENT REGARDING PRIOR DISCLOSURES BY THE INVENTOR OR A JOINT INVENTOR UNDER 37 C.F.R 1.77(B)(6)

Part of the subject matter of the invention described in the present application was published by the inventors, Yu-Fa WU and Yow-Fu TSAI in an article titled "Assistance of the c-7,8-picoloyl moiety for directing the glycosyl acceptors into the α-orientation for the glycosylation of sialyl donors." The article was published on Jul. 28, 2017 in Org. Lett. 19:4171-4174. The publication was made by and/or originated from the inventive entity of the present invention, and the entirety of this article is incorporated herein by reference. A copy of the article is provided in a concurrently filed Information Disclosure Statement pursuant to the guidance of 78 Fed. Reg. 11076 (Feb. 14, 2013)."

BACKGROUND OF THE INVENTION

1. Field of the Invention

The present disclosure in general relates to the synthesis of sialosides. Specifically, the present disclosure relates to a novel sialyl donor, which help directing α-stereoselective sialyation during the synthesis of a natural sialoside; and the use of the novel sialyl donor for the synthesis of sialoside.

2. Description of Related Art

Sialic acids are a diverse family of carboxylated sugars with a skeleton of nine carbon atoms, and are widely expressed on the cell surfaces of all animals and are frequently located at the terminal position of glycoconjugates on the cell surface. They play important functional roles in various biological and pathological processes, such as cell-cell adhesion and recognition, cell differentiation, signal transduction, and tumor metastasis. Hence, sialic acid glycosides and their oligomers have potential applications in medicine, and the synthesis of glycoconjugates containing sialic acid is very important.

Natural sialosides are in α-anomeric structures. Because of the presence of the C-1 carboxyl group at the tertiary anomeric center and the lack of a stereocontrolling group at C-3 to direct α-stereoselective sialyation, achieving high α-stereoselectivity of the glycosylation of sialic acid donors with high product yield remains a challenge. Many attempts have been tried to develop efficient strategies and/or methodologies for α-sialylation, yet none of them produce satisfactory results.

In view of the above, there exists in this art a need of an improved strategy for stereo-selectively synthesizing sialosides that are in α-anomeric structures without compromising the production yield.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In general, the present disclosure relates to the discovery of a new and unique sialyl donor, which help directing α-stereoselective sialyation at C-3 position during the synthesis of a natural sialoside, thus achieves the high α-stereoselectivity of the glycosylation of the sialic donor with improved product yield. Accordingly, the present disclosure also provides a method of synthesizing a sialoside by use of the novel sialyl donor.

The first aspect of the present disclosure aims at providing a sialyl donor having the structure of formula (I),

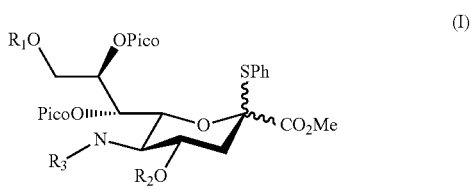

wherein,
$R_1$ and $R_2$ are independently benzoyl, toluenesulfonyl, pivaloyl or acetyl optionally substituted with a halogen; and
$R_3$ is acetyl or —(O)CCH$_2$OH.

According to one preferred embodiment, in the formula (I), $R_1$ and $R_2$ are independently benzoyl, and $R_3$ is acetyl.

According to another preferred embodiment, in the formula (I), $R_1$ and $R_2$ are independently benzoyl, and $R_3$ is —(O)CCH$_2$OH.

The second aspect of the present disclosure pertains to a method for synthesizing a sialoside. The method includes steps of:

(a) coupling a sialyl donor with a glycosyl acceptor having a primary hydroxyl group in the presence of N-iodosuccinimide (NIS) and trifluoromethanesulfonic acid (TfOH) under suitable conditions; and (b) isolating the sialoside, which has an α-glycosidic linkage;

wherein, the silalyl donor has the structure of formula (I),

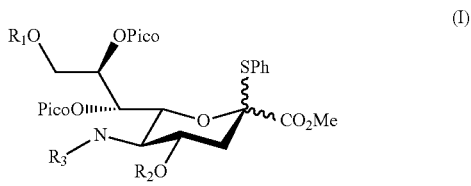

in which $R_1$ and $R_2$ are independently benzoyl, toluenesulfonyl, pivaloyl, or acetyl optionally substituted with a halogen; and $R_3$ is acetyl or —(O)CCH$_2$OH.

According to some embodiments of the present disclosure, in the step (a) of the present method, the coupling reaction is performed in a solvent selected from the group consisting of, CH$_3$CN, CH$_3$Cl, and CH$_2$Cl$_2$ at a temperature between −20° C. to −60° C. Preferably, the coupling is performed in CH$_2$Cl$_2$ at the temperature of −40° C.

According to optional embodiments of the present disclosure, in the step (a) of the present method, the coupling reaction is conducted in the presence of a powdered molecular sieve.

Many of the attendant features and advantages of the present disclosure will become better understood with reference to the following detailed description considered in connection with the accompanying drawings.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

In the present disclosure, the term "Pic" refers to picolinyl or 2-pyridylmethyl group; whereas the term "Pico" refers to picoloyl or 2-pyridinecarbony group.

The term "halo" or "halogen" refers to fluorine (fluoro, —F), chlorine (chloro, —Cl), bromine (bromo, —Br), or iodine (iodo, —I).

Unless otherwise specified, each instance of a benzoyl, toluenesulfonyl, pivaloyl, or acetyl group is independently optionally substituted, i.e., unsubstituted (an "unsubstituted benzoyl") or substituted (a "substituted acetyl") with one or more substituents. The term "substituted," when used to describe a chemical structure or moiety, refers to a derivative of that structure or moiety wherein one or more of its hydrogen atoms is substituted with one or more of: halo or hydroxyl.

It should also be noted that names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a," "and," and "the" are used herein to include plural referents unless the context clearly dictates otherwise.

2. Detail Description of the Invention

The present disclosure is based, at least in part, on the discovery of a novel sialyl donor capable of directing a glycosyl acceptor into α-orientation. Surprisingly, this novel sialyl donor can be glycosylated with excellent α-stereoselectivity (98-100%) in the presence of N-iodosuccinimide and catalytic trifluoromethanesufonic acid at −20° C. to −60° C. in a suitable solvent (e.g., $CH_2Cl_2$ and etc). The glycosylation reaction can be accomplished in a short period of time (e.g., 0.5 hrs) to give predominately a product with α-anomeric structure. Accordingly, the present novel sialyl donor is useful for stereoselectively synthesizing natural sialosides having an α-anomeric structure, which includes but is not limited to, the ganglioside Hp-s1.

To identify preferred sialyl donor capable of directing a glycosyl acceptor into α-orientation, potential sialyl donors were synthesized and reacted with a glycosyl acceptor, respectively. Accordingly, the first aspect in the present disclosure is directed to a novel sialyl donor having the structure of formula (I),

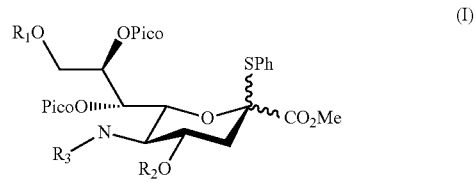

(I)

wherein, $R_1$ and $R_2$ are independently benzoyl, toluenesulfonyl, pivaloyl, or acetyl optionally substituted with a halogen; and $R_3$ is acetyl or —(O)$CCH_2OH$.

According to embodiments of the present disclosure, the sialyl donor of formula (I) may be any of the followings:

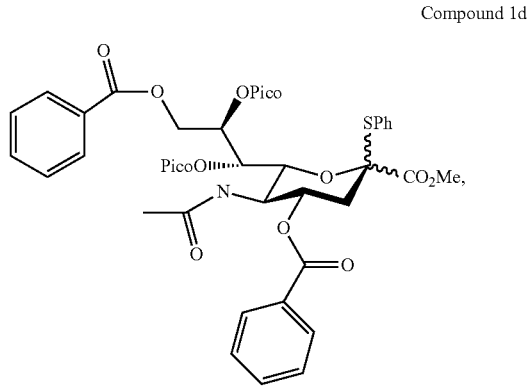

Compound 1d

-continued
compound 1d-2
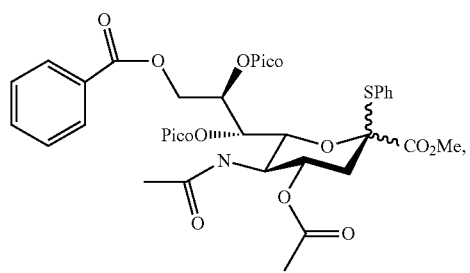
compound 1d-3
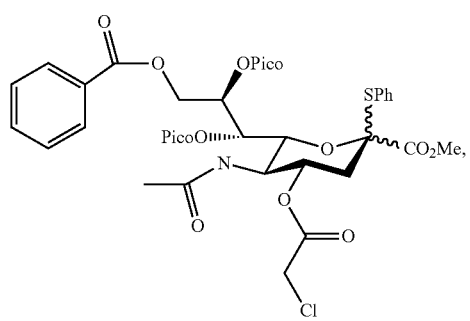
Compound 1d-4
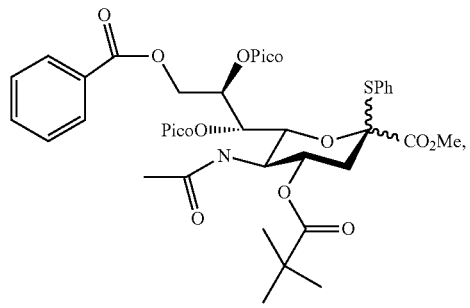
compound 1d-5
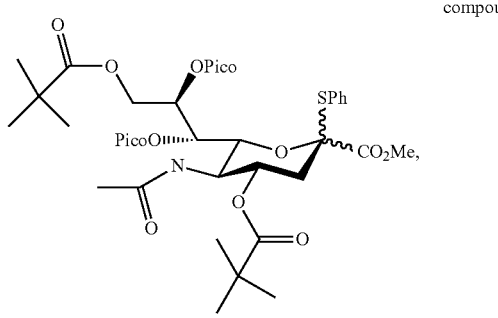
compound 1d-6
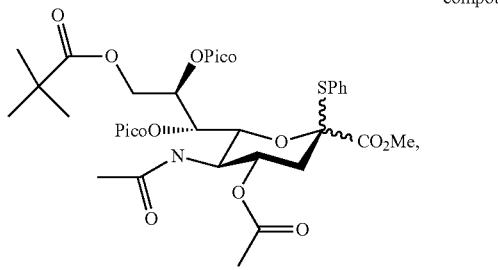
-continued
Compound 1d-7
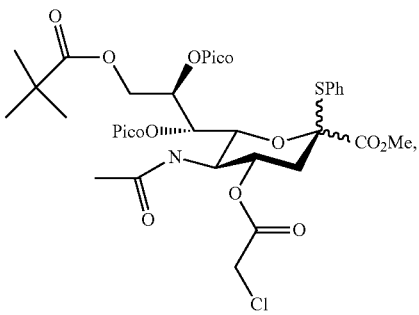
compound 1d-8
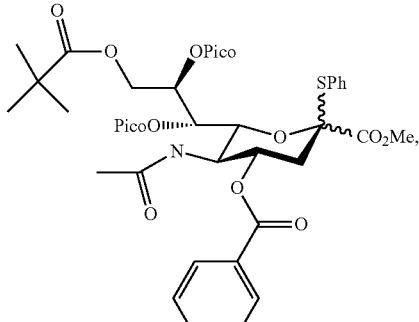
compound 1d-9
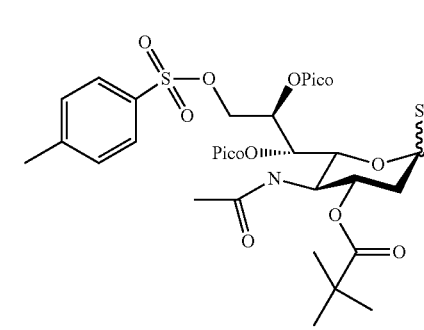
Compound 1d-10
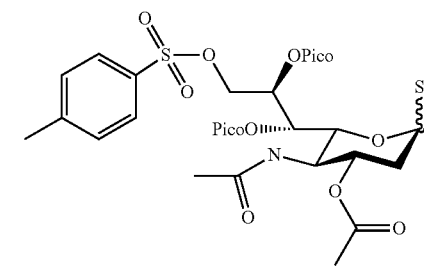
compound 1d-11
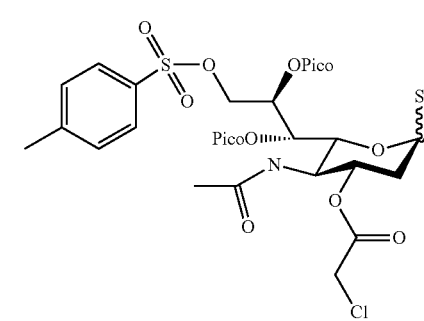

compound 1d-12
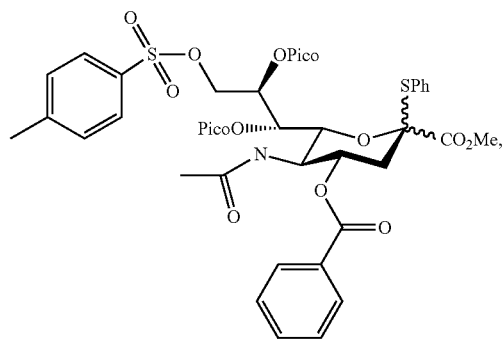
Compound 1h
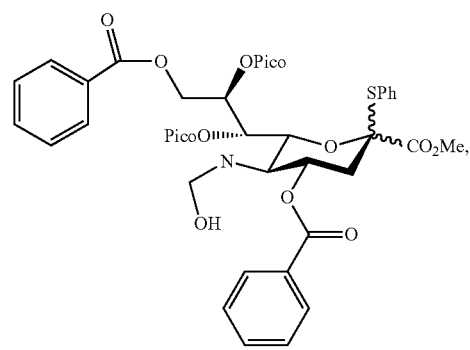
compound 1h-2
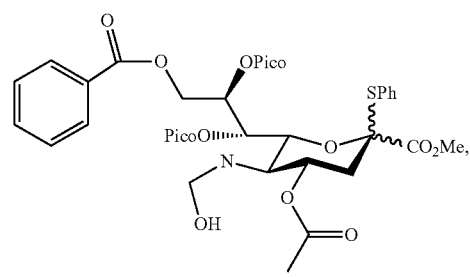
compound 1h-3
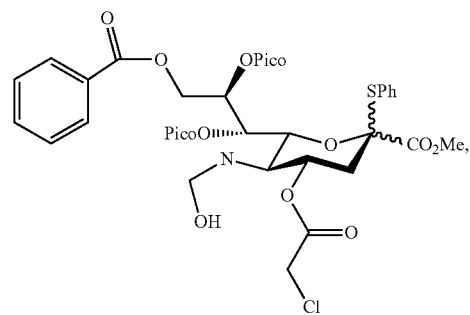
Compound 1h-4
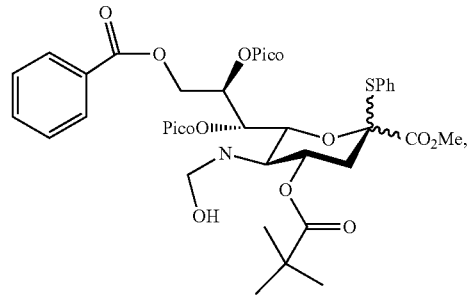
compound 1h-5
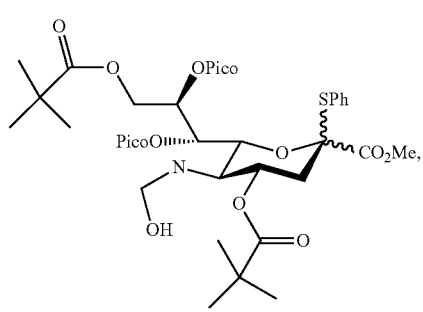
compound 1h-6
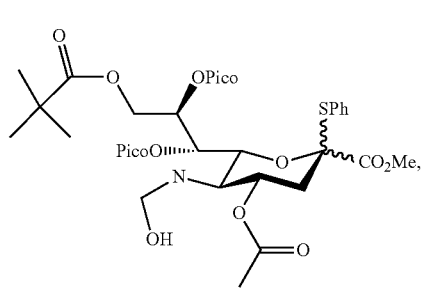
Compound 1h-7
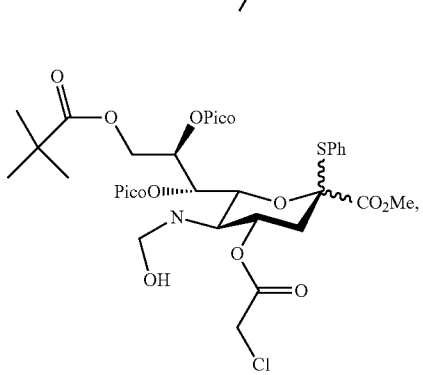
compound 1h-8
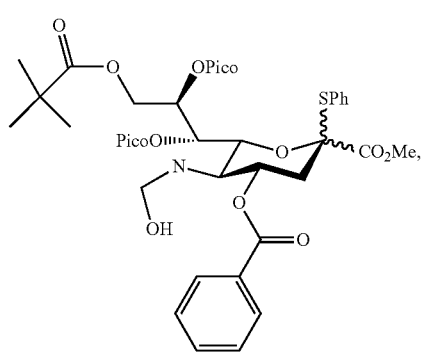

-continued compound 1h-9

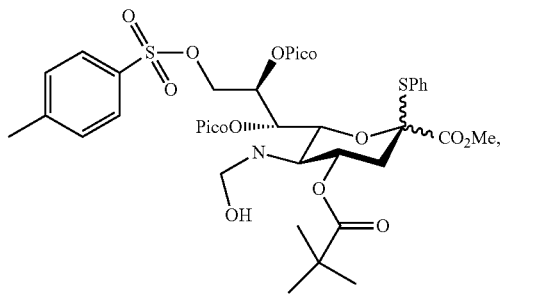

Compound 1h-10

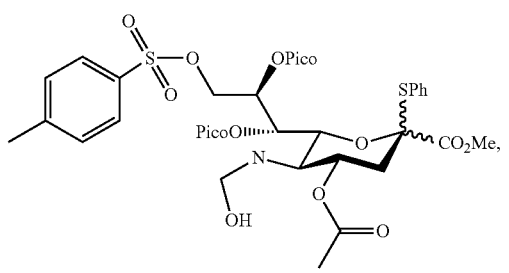

compound 1h-11

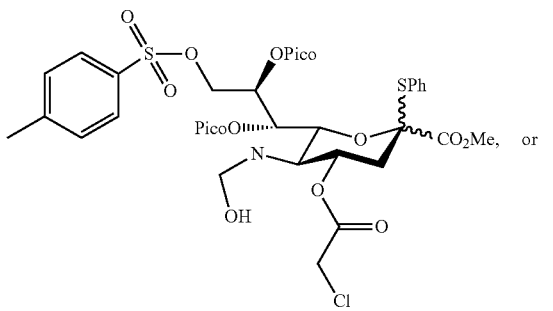

compound 1h-12

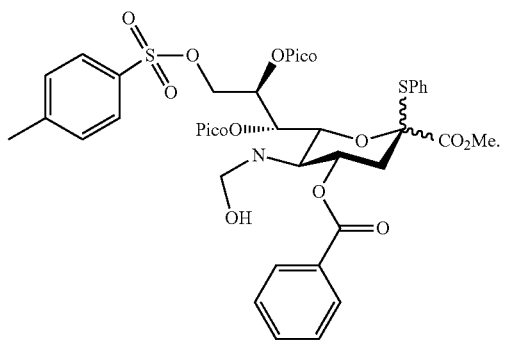

In one preferred embodiment, in the formula (I), $R_1$ and $R_2$ are independently benzoyl, and $R_3$ is acetyl, which gives rise to a sialyl donor (i.e., compound 1d) that when reacted with a glycosyl acceptor will give rise to α-anomer only (i.e., the α-stereoselectivity is 100%).

In another preferred embodiment, in the formula (I), $R_1$ and $R_2$ are independently benzoyl, and $R_3$ is —(O)CCH$_2$OH (i.e., compound 1h).

The second aspect of the present disclosure aims at providing a method for synthesizing a sialoside. The method includes steps of:

(a) coupling the sialyl donor with a glycosyl acceptor having a primary hydroxyl group in the presence of N-iodosuccinimide (NIS) and trifluoromethanesulfonic acid (TfOH) under suitable conditions; and (b) isolating the sialoside, which has an α-glycosidic linkage;

wherein, the silalyl donor has the structure of formula (I),

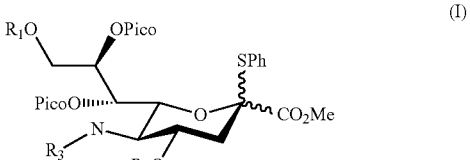

(I)

wherein, $R_1$ and $R_2$ are independently benzoyl, toluenesulfonyl, pivaloyl, or acetyl optionally substituted with a halogen; and $R_3$ is acetyl or —(O)CCH$_2$OH.

According to some embodiments of the present disclosure, in the step (a) of the present method, the coupling reaction is performed in a solvent selected from the group consisting of, CH$_3$CN, CH$_3$Cl, and CH$_2$Cl$_2$ at a temperature between −20° C. to −60° C.

In one embodiment of the present disclosure, the coupling reaction of the step (a) is conducted in the presence of NIS and TfOH in CH$_2$Cl$_2$ at the temperature of −20° C. The reaction is completed within 0.5 hr, with a moderate α-stereoselectivity, in which the amount of the disaccharide α-anomer is about 5 folds over that of the β-anomer with a yield about 24%.

In another embodiment of the present disclosure, the coupling reaction of the step (a) is conducted in the presence of NIS and TfOH in CH$_2$Cl$_2$ at the temperature of −40° C. The reaction is completed within 2 hrs with excellent α-stereoselectivity, in which only α-anomer is produced, and the yield is about 70%.

In still another embodiment of the present disclosure, the coupling reaction of the step (a) is conducted in the presence of NIS and TfOH in CH$_2$Cl$_2$ at the temperature of −60° C. The reaction is completed within 5 hrs with excellent α-stereoselectivity, in which only α-anomer is produced, and the yield is about 69%.

In further embodiment of the present disclosure, the coupling reaction of the step (a) is conducted in the presence of NIS and TfOH in CH$_3$CN at the temperature of −40° C. The reaction is completed within 0.5 hr with excellent α-stereoselectivity, in which only α-anomer is produced, and the yield is about 56%.

In still further embodiment of the present disclosure, the coupling reaction of the step (a) is conducted in the presence of NIS and TfOH in CHCl$_3$ at the temperature of −40° C. The reaction is accomplished within 0.5 hrs with excellent α-stereoselectivity, in which only α-anomer is produced, yet the yield is merely 20%.

Optionally or additionally, the coupling reaction in the step (a) of the present method is conducted in the presence of a powdered molecular sieve (e.g., MS-3A).

Preferably, the disaccharide thus produced in the step (a) has an α-anomeric structure, and may be isolated by any suitable method (e.g., column chromatography) in the step (b).

According to some embodiments of the present disclosure, to identify the best glycosyl acceptor suitable for coupling to the sialyl donor of the present disclosure, potential glycosyl acceptors were synthesized and respectively reacted with the sialyl donor of the present disclosure at suitable condition, for example, in the presence of NIS and TfOH in CH$_2$Cl$_2$ at −40° C. with the optional addition of MS-3A as described above. It was found that, to achieve higher α-stereoselectivity, the coupling between the sialy donor and the glycosyl acceptor is preferably occurred at a primary hydroxyl group (or primary alcohol), accordingly, the glycosyl acceptor preferably comprises a primary alcohol in its structure. In certain example, a sugar alcohol having a secondary hydroxyl group (e.g., compound 5e) is used as a glycosyl acceptor, yet no coupling reaction occurs between the sialyl donor of the present disclosure and the sugar alcohol.

It is a further aspect of the present disclosure to provide a method of synthesizing a natural ganglioside that comprises an α-anomeric structure. The method is characterized in having the sialyl donor of formula (I) as a starting material to direct a glycosyl acceptor into α-orientation. In general, depending on the particular ganglioside to be synthesized, the sialyl donor of formula (I) is reacted with a glycosyl acceptor having a primary hydroxyl group at the preferred conditions identified in the present disclosure (i.e., in the presence of NIS and TfOH in CH$_2$Cl$_2$ at −40° C. with the optional addition of MS-3A), so as to produce a disaccharide having an α-glycosidic linkage, which can then be used to produce the desired ganglioside by use of any conventional synthesizing schemes.

According to one preferred embodiment of the present disclosure, the sialyl donor of formula (I) is used as a starting material for the production of Hp-s1. Preferably, the sialyl donor of formula (I) is first reacted with S-thiazolyl acceptor in the presence of NIS and TfOH in CH$_2$Cl$_2$ at −40° C. with the addition of MS-3A. The reaction will give rise to a disaccharide having only α-anomeric structure, which is deprotected (i.e., by removing the picoloyl group on the disaccharide), and further reacted with phytoceramide to give protected Hp-s1. The protected Hp-s1 is then subjected to sequential deprotection reactions that include, deisopropylidenenation, debenzylation, deacetylation, and saponification, to produce the desired ganglioside Hp-s1.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLES

Materials and Methods
Cell Lines and Cell Culture.
A549 were obtained from the American Type Culture Collection (ATCC; Manassas, Va., USA). A549 cells were maintained in Dulbecco's minimal essential medium (DMEM) supplemented with 1.5 g/L sodium bicarbonate, 10% fetal bovine serum (FBS), 1.0% antibiotic-antimycotic, L-glutamine (2.0×10$^{-3}$ M), and 1.0% nonessential amino acids. The cell number and viability of the cells were determined by the trypan blue exclusion method and Alamar Blue assay, respectively.

Example 1 Screening of Sialyl Donor and Evaluating the Optimal Condition for the Glycosylation of the Sialyl Donor To identify a potential sialyl donor suitable for directing a glycosyl acceptor into α-orientation, various sialyl donor s were synthesized (see Example 1.1) and coupled with a glucosyl acceptor under suitable conditions, the products were then isolated and analyzed for its α-stereoselectivity (see Example 1.2). Compounds 1d and 1h were identified to be the preferred sialyl donor with high product yield.

1.1 Preparation of Sialyl Donor 1.1.1 Preparation of the Sialyl Donor 1c

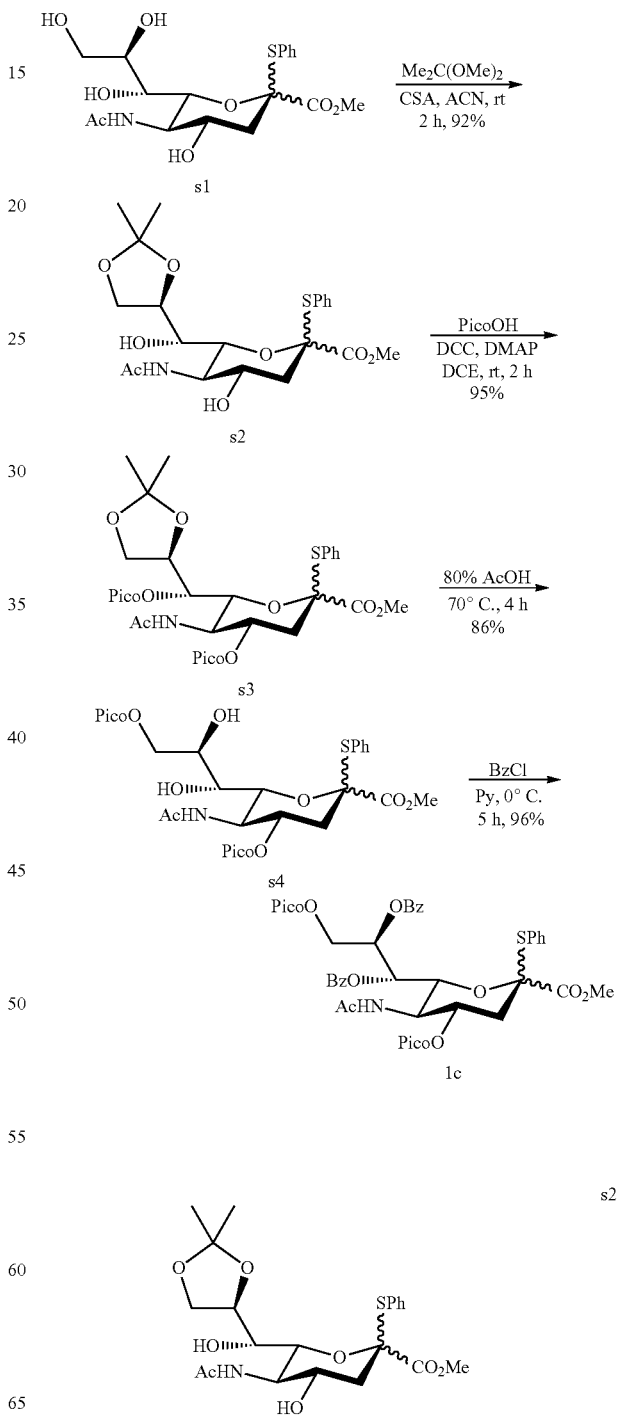

Methyl (phenyl 5-acetamido-3,5-dideoxy-8,9-O-isopropylidene-2-thio-D-glycero-D-galacto-2-nonulopyranosid)onate (s2)

To a stirring solution of compound s1 (10.006 g, 24.10 mmol) in dry acetonitrile (240 mL) was added 2,2-dimethoxypropane (4.4 mL, 36.15 mmol) and CSA (4.454 g, 19.28 mmol) at 0° C. The mixture was warmed to room temperature and continuously stirred at this temperature for 2 h. The reaction mixture was carefully quenched with Et$_3$N (5.0 mL) and concentrated in vacuo. The observed yellow syrup was purified by flash column chromatography on silica gel using MeOH and CH$_2$Cl$_2$ (1:15, v/v) as the eluent to give 10.109 g of a white solid s2 in 92% yield: R$_f$=0.25 (MeOH:CH$_2$Cl$_2$=1:15 (v/v)); FT-IR (neat) v$_{max}$ 3299, 3083, 2993, 2953, 1737, 1660, 1557, 1439, 1377, 1263, 1202, 1135, 1065, 901, 756, 696, 666, 609 cm$^{-1}$; $^1$H NMR (400 MHz, CD$_3$OD) δ 7.55-7.53 (m, 2H), 7.39-7.36 (m, 1H), 7.32-7.28 (m, 2H), 4.34 (dd, J=10.5, 0.9 Hz, 1H), 4.16-4.08 (m, 2H), 3.98-3.82 (m, 3H), 3.56 (dd, J=7.5, 0.9 Hz, 1H), 3.51 (s, 3H), 2.69 (dd, J=13.6, 4.7 Hz, 1H), 2.02 (s, 3H), 1.95 (dd, J=13.6, 11.8 Hz, 1H), 1.39 (s, 3H), 1.38 (s, 3H), 1.30 (s, 3H), 1.21 (s, 3H); $^{13}$C NMR (100 MHz, CD$_3$OD) δ 173.4 (C), 169.2 (C), 136.0 (CH), 129.8 (C), 129.3 (CH), 128.5 (CH), 108.8 (C), 90.0 (C), 74.7 (CH), 72.6 (CH), 70.0 (CH), 66.6 (CH$_2$), 66.4 (CH), 52.7 (CH), 51.8 (CH$_3$), 48.5 (CH$_3$), 40.9 (CH$_2$), 25.9 (CH$_3$), 24.7 (CH$_3$), 21.6 (CH$_3$); HRMS-ESI [M+Na]$^+$ Calcd for C$_{21}$H$_{29}$NO$_8$SNa 478.1506, Found 478.1499.

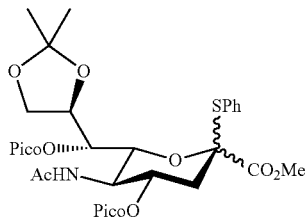

s3

Methyl (phenyl 5-acetamido-3,5-dideoxy-8,9-O-isopropylidene-4,7-di-O-picoloyl-2-thio-D-glycero-D-galacto-2-nonulopyranosid)onate (s3)

To a stirring solution of compound s2 (10.003 g, 22.00 mmol) in dry dichloroethane (73 mL) was added 2-picolinic acid (6.765 g, 55.00 mmol), DMAP (0.268 g, 2.20 mmol) and DCC (10 mL, 66.00 mmol) at 0° C. The mixture was warmed to room temperature and continuously stirred at this temperature for 2 h. The reaction mixture was filtered through a short pad of Celite and concentrated in vacuo. The observed black solid was purified by flash column chromatography on silica gel using acetone and ethyl acetate (1:1, v/v) as the eluent to give 13.919 g of a white solid s3 in 92% yield: R$_f$=0.23 (acetone:ethyl acetate=1:1 (v/v)); FT-IR (neat) v$_{max}$ 3330, 2988, 1739, 1675, 1581, 1543, 1438, 1373, 1307, 1245, 1213, 1131, 1089, 1053, 994, 751, 701 cm$^{-1}$; $^1$H NMR (400 MHz, CDCl$_3$) δ 8.77 (d, J=4.0 Hz, 1H), 8.73 (d, J=4.0 Hz, 1H), 8.10 (d, J=7.8 Hz, 1H), 8.03 (d, J=7.8 Hz, 1H), 7.84 (td, J=7.8, 1.7 Hz, 1H), 7.79 (td, J=7.8, 1.7 Hz, 1H), 7.59-7.57 (m, 2H), 7.49 (m, 5H), 6.08 (ddd, J=11.6, 10.8, 4.9 Hz, 1H), 5.94-5.88 (m, 1H), 5.81-5.80 (m, 1H), 5.11 (dd, J=10.5, 1.8 Hz, 1H), 4.14-4.06 (m, 2H), 3.98-3.91 (m, 1H), 3.73 (dd, J=7.2, 5.9 Hz, 1H), 3.65 (s, 3H), 2.93 (dd, J=13.7, 4.9 Hz, 1H), 2.26 (dd, J=13.7, 11.6 Hz, 1H), 1.90 (s, 3H), 1.29 (s, 3H), 1.21 (s, 3H); $^{13}$C NMR (75 MHz, CDCl$_3$) δ 170.7 (C), 170.6 (C), 168.3 (C), 164.4 (C), 164.3 (C), 150.0 (CH), 149.9 (CH), 147.6 (C), 147.2 (C), 137.2 (CH), 137.1 (CH), 136.9 (CH), 136.3 (CH), 129.8 (CH), 129.3 (CH), 128.9 (CH), 127.2 (CH), 127.0 (CH), 125.6 (CH), 125.5 (CH), 108.5 (C), 108.4 (C), 88.8 (C), 87.7 (C), 75.4 (CH), 71.7 (CH), 71.0 (CH), 70.7 (CH), 70.2 (CH), 65.8 (CH$_2$), 65.5 (CH$_2$), 52.9 (CH$_3$), 52.5 (CH$_3$), 50.6 (CH), 38.1 (CH$_2$), 26.3 (CH$_3$), 26.2 (CH$_3$), 25.4 (CH$_3$), 25.1 (CH$_3$), 23.3 (CH$_3$); HRMS-ESI [M+Na]$^+$ Calcd for C$_{33}$H$_{35}$N$_3$O$_{10}$SNa 688.1935, Found 688.1918.

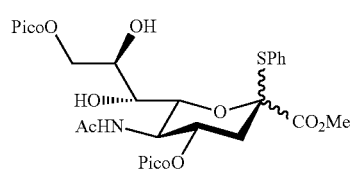

s4

Methyl (phenyl 5-acetamido-3,5-dideoxy-4,9-di-O-picoloyl-2-thio-D-glycero-D-galacto-non-2-ulopyranoside)onate (s4)

The isopropylidene acetal s3 (8.000 g, 12.79 mmol) was dissolved in a solution of 80% aqueous AcOH (120 mL) at 0° C. and then the mixture was continuously stirred for 4 h at 70° C. The reaction mixture was co-evaporated with toluene to give a white solid residue. After recrystallization (MeOH/CH$_2$Cl$_2$) of the afforded 6.467 g of s4 as a white solid compound in 86% yield: R$_f$=0.28 (MeOH:CH$_2$Cl$_2$=1:9 (v/v)); FT-IR (neat) v$_{max}$ 3311, 3064, 3009, 2954, 1732, 1659, 1555, 1439, 1375, 1309, 1246, 1136, 1089, 1047, 998, 752, 701 cm$^{-1}$; $^1$H NMR (400 MHz, CD$_3$OD) δ 8.69-8.68 (m, 2H), 8.22 (dt, J=7.9, 0.9 Hz, 1H), 8.09 (dt, J=7.9, 0.9 Hz, 1H), 8.00 (td, J=7.8, 1.6 Hz, 1H), 7.91 (td, J=7.8, 1.6 Hz, 1H), 7.65-7.54 (m, 4H), 7.36-7.31 (m, 3H), 5.68 (ddd, J=11.6, 8.4, 4.8 Hz, 1H), 4.75-4.69 (m, 2H), 4.43-4.36 (m, 2H), 4.16 (ddd, J=9.0, 6.6, 2.3 Hz, 1H), 3.7 (dd, J=9.0, 0.8 Hz, 1H), 3.50 (s, 3H), 2.94 (dd, J=13.5, 4.8 Hz, 1H), 2.28 (dd, J=13.5, 11.6 Hz, 1H), 1.99 (s, 3H); $^{13}$C NMR (75 MHz, CD$_3$OD) δ 173.8 (C), 173.5 (C), 172.9 (C), 169.2 (C), 168.3 (C), 164.8 (C), 164.7 (C), 164.6 (C), 150.2 (CH), 149.7 (CH), 149.2 (CH), 147.8 (C), 147.6 (C), 146.9 (C), 137.7 (CH), 137.5 (CH), 137.3 (CH), 136.9 (CH), 136.1 (CH), 129.5 (CH), 129.5 (CH), 128.9 (CH), 128.8 (CH), 127.5 (CH), 127.3 (CH), 125.6 (CH), 125.3 (CH), 89.6 (C), 72.5 (CH), 70.5 (CH), 69.4 (CH), 68.7 (CH$_2$), 68.3 (CH), 52.5 (CH$_3$), 50.8 (CH$_3$), 38.0 (CH$_2$), 23.0 (CH$_3$), 22.9 (CH$_3$); HRMS-ESI [M+Na]$^+$ Calcd for C$_{30}$H$_{31}$N$_3$O$_{10}$SNa 648.1622, Found 648.1629.

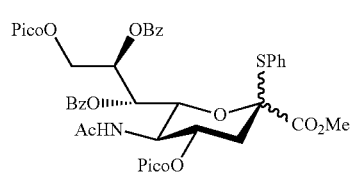

1c

Methyl (phenyl 5-acetamido-7,8-di-O-benzoyl-3,5-dideoxy-4,9-di-O-picoloyl-2-thio-D-glycero-D-galacto-non-2-ulopyranoside)onate (1c)

To a stirring solution of compound s4 (0.200 g, 0.32 mmol) in dry pyridine (1.6 mL) was added benzoyl chloride (0.08 mL, 0.70 mmol) at 0° C. The mixture was continuously stirred at this temperature for 5 h. The reaction mixture was quenched with water at ice bath, extracted with ethyl acetate, washed with cold saturated aqueous $K_2CO_3$ and brine, dried over $MgSO_4$, and concentrated in vacuo. The resulting white solid residue was purified by flash column chromatography on silica gel using ethyl acetate and n-hexane (2.5:1, v/v) as the eluent to get 0.255 g of 1c as a white solid compound in 96% yield: $R_f$=0.28 (ethyl acetate: n-hexane=3:1 (v/v)); FT-IR (neat) $v_{max}$ 3324, 3066, 2919, 2852, 1731, 1674, 1546, 1443, 1369, 1266, 1097, 1035, 894, 754, 712, 610 cm$^{-1}$; $^1$H NMR (400 MHz, CDCl$_3$) δ 8.92 (d, J=4.1 Hz, 1H), 8.77 (d, J=4.1 Hz, 1H), 8.07-7.97 (m, 6H), 7.85-7.78 (m, 2H), 7.60 (t, J=7.4 Hz, 1H), 7.54-7.44 (m, 5H), 7.40-7.36 (m, 4H), 7.14-7.09 (m, 3H), 6.97 (d, J=9.6 Hz, 1H), 6.06 (dd, J=4.2, 1.8 Hz, 1H), 5.91 (ddd, J=13.5, 10.1, 4.9 Hz, 1H), 5.71 (ddd, J=6.5, 4.8, 1.8 Hz, 1H), 5.12 (dd, J=10.1, 4.2 Hz, 1H), 5.07 (dd, J=11.8, 4.8 Hz, 1H), 4.58 (dd, J=11.8, 7.1 Hz, 1H), 4.38 (q, J=10.1 Hz, 1H), 3.54 (s, 3H), 2.84 (dd, J=13.5, 4.9 Hz, 1H), 2.35 (dd, J=13.5, 11.8 Hz, 1H), 1.85 (s, 3H); $^{13}$C NMR (100 MHz, CDCl$_3$) δ 170.4 (C), 168.0 (C), 165.8 (C), 164.4 (C), 164.4 (C), 163.8 (C), 150.0 (CH), 149.9 (CH), 147.3 (C), 147.0 (C), 137.3 (CH), 136.9 (CH), 136.1 (CH), 133.1 (CH), 133.0 (CH), 129.8 (CH), 129.7 (CH), 129.6 (C), 129.4 (CH), 129.3 (C), 129.0 (C), 128.8 (CH), 128.3 (CH), 128.3 (CH), 127.1 (CH), 126.8 (CH), 125.7 (CH), 125.0 (CH), 88.9 (C), 73.0 (CH), 72.7 (CH), 71.0 (CH), 70.8 (CH), 63.8 (CH$_2$), 52.3 (CH$_3$), 49.5 (CH), 37.5 (CH$_2$), 23.0 (CH$_3$); HRMS-ESI [M+Na]$^+$ Calcd for $C_{44}H_{39}N_3O_{12}SNa$ 856.2147, Found 856.2146.

1.1.2 Preparation of the Sialyl Donor 1a and 1e

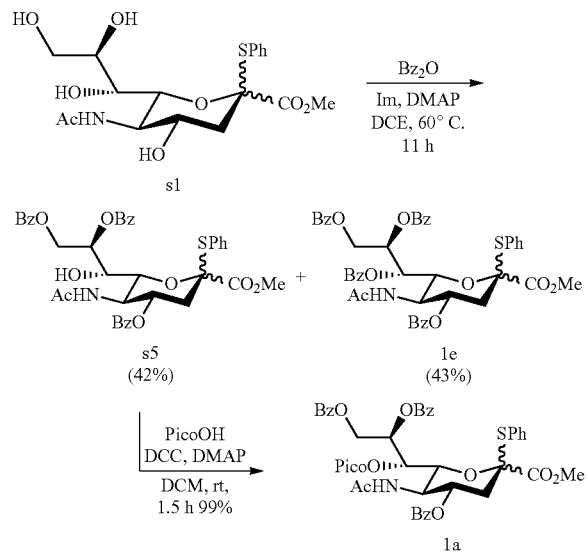

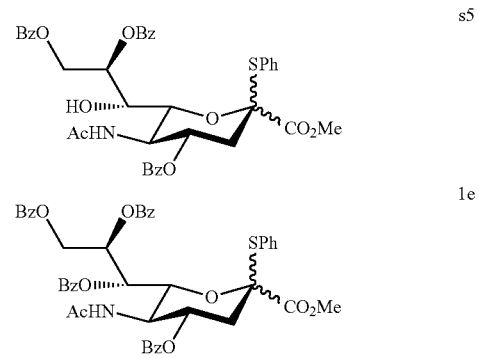

Methyl (phenyl 5-acetamido-4,8,9-tri-O-benzoyl-3,5-dideoxy-2-thio-D-glycero-D-galacto-non-2-ulopyranoside)onate (s5) and Methyl (phenyl 5-acetamido-4,7,8,9-tetra-O-benzoyl-3,5-dideoxy-2-thio-D-glycero-D-galacto-non-2-ulopyranoside)onate (1e)

To a stirring solution of compound s1 (0.503 g, 1.20 mmol), Im (0.410 g, 6.02 mmol), DMAP (0.073 g, 0.60 mmol) in dry dichloroethane (6.0 mL) was added benzoic anhydride (1.085 g, 4.80 mmol) at 0° C. The mixture was warmed to 60° C. and continuously stirred at this temperature for 11 h. The reaction mixture was quenched with 6N HCl at ice bath, extracted with ethyl acetate, washed with cold saturated aqueous $K_2CO_3$ and brine, dried over $MgSO_4$, and concentrated in vacuo. The resulting white solid residue was purified by flash column chromatography on silica gel using ethyl acetate and n-hexane (1:2, v/v) as the eluent to get 0.368 g of s5 as a white solid compound in 42% yield, and 0.431 g of a white solid compound 1e in 43% yield: s5: $R_f$=0.38 (ethyl acetate:n-hexane=1:1 (v/v)); FT-IR (neat) $v_{max}$ 3355, 3066, 2954, 1721, 1663, 1602, 1548, 1448, 1373, 1269, 1172, 1112, 1070, 1027, 755, 712 cm$^{-1}$; $^1$H NMR (400 MHz, CDCl$_3$) δ 8.11-8.08 (m, 2H), 8.02-8.00 (m, 2H), 7.92-7.89 (m, 2H), 7.62-7.37 (m, 11H), 7.20-7.16 (m, 2H), 7.06-7.02 (m, 1H), 6.41 (d, J=8.0 Hz, 1H), 5.76 (ddd, J=11.8, 10.3, 4.8 Hz, 1H), 5.48-5.45 (m, 1H), 4.95 (dd, J=12.2, 2.2 Hz, 1H), 4.92 (d, J=4.1 Hz, 1H), 4.66 (dd, J=12.2, 8.2 Hz, 1H), 4.48 (dd, J=10.3, 1.4 Hz, 1H), 4.24-4.17 (m, 1H), 4.10 (bs, 1H), 3.55 (s, 3H), 2.87 (dd, J=13.8, 4.8 Hz, 1H), 2.41 (dd, J=13.8, 11.8 Hz, 1H), 1.96 (s, 3H); $^{13}$C NMR (75 MHz, CDCl$_3$) δ 173.2 (C), 168.6 (C), 167.1 (C), 166.4 (C), 165.9 (C), 136.1 (CH), 133.8 (CH), 133.2 (CH), 132.8 (CH), 130.3 (CH), 130.0 (CH), 129.8 (CH), 129.7 (CH), 129.6 (CH), 129.0 (CH), 128.9 (CH), 128.6 (CH), 128.6 (CH), 128.4 (CH), 128.3 (CH), 89.3 (C), 74.8 (CH), 74.4 (CH), 69.9 (CH), 69.2 (CH), 64.0 (CH$_2$), 52.6 (CH$_3$), 51.8 (CH), 37.8 (CH$_2$), 23.1 (CH$_3$); HRMS-ESI [M+Na]$^+$ Calcd for $C_{39}H_{37}NO_{11}SNa$ 750.1980, Found 750.1969; 1e: $R_f$=0.50 (ethyl acetate:n-hexane=1:1 (v/v)); FT-IR (neat) $v_{max}$ 3372, 3066, 1724, 1601, 1536, 1449, 1369, 1265, 1175, 1105, 1070, 1026, 892, 755, 712 cm$^{-1}$; $^1$H NMR (400 MHz, CDCl$_3$) δ 8.12-7.93 (m, 9H), 7.65-7.31 (m, 15H), 7.24-7.22 (m, 1H), 7.11-7.07 (m, 1H), 6.03-6.01 (m, 1H), 5.86-5.86 (m, 1H), 5.76-5.69 (m, 2H), 5.56-5.53 (m, 2H), 5.29-5.22 (m, 1H), 5.03-4.94 (m, 3H), 4.68-4.64 (m, 1H), 4.52 (dd, J=12.2, 8.8 Hz, 1H), 4.37 (q, J=10.5 Hz, 1H), 4.28 (d, J=10.5 Hz, 1H), 4.14 (q, J=9.9 Hz, 1H), 3.65 (s, 3H), 3.42 (s, 3H), 3.06 (dd, J=12.8, 4.7 Hz, 1H), 2.95 (dd, J=13.8, 4.7 Hz, 1H), 2.32 (dd, J=13.8, 11.8 Hz, 1H), 2.12 (dd, J=12.8, 11.8 Hz, 1H), 1.81 (s, 3H), 1.79 (s, 3H); $^{13}$C NMR (75 MHz, CDCl$_3$) δ 170.6 (C), 170.6 (C), 168.8 (C), 168.6 (C), 166.9 (C), 166.6 (C), 166.5 (C), 166.3 (C), 165.9 (C), 165.9 (C), 165.5 (C), 136.9 (CH), 136.2 (CH), 133.5 (CH), 133.5 (CH), 133.4 (CH), 133.4 (CH), 133.3 (CH), 133.1 (CH), 133.0 (CH), 130.1 (CH), 130.0 (CH), 129.9 (CH), 129.8 (CH), 129.8 (CH), 129.7 (CH), 129.7 (CH), 129.6 (CH), 129.3 (CH), 129.2 (CH), 129.0 (CH), 128.8 (CH), 128.6 (CH), 128.5 (CH), 128.4 (CH), 128.3 (CH), 89.2 (C), 88.0 (C), 75.6 (CH), 74.2 (CH), 73.5 (CH), 71.9 (CH), 70.8 (CH), 70.6 (CH), 70.4 (CH), 69.3 (CH), 63.6 (CH$_2$), 63.2 (CH$_2$), 52.8 (CH$_3$), 52.7 (CH$_3$), 49.6 (CH), 38.3 (CH$_2$), 38.0 (CH$_2$), 23.1 (CH$_3$); HRMS-ESI [M+Na]$^+$ Calcd for C$_{46}$H$_{41}$NO$_{12}$SNa 854.2242, Found 854.2253.

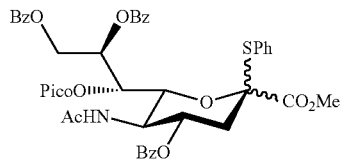

1a

Methyl (phenyl 5-acetamido-4,8,9-tri-O-benzoyl-3, 5-dideoxy-7-O-picoloyl-2-thio-D-glycero-D-galacto-non-2-ulopyranoside)onate (1a)

To a stirring solution of compound s5 (0.305 g, 0.41 mmol) in dry CH$_2$Cl$_2$ (2.0 mL) was added 2-picolinic acid (0.076 g, 0.62 mmol), DMAP (0.005 g, 0.04 mmol) and DCC (0.130 g, 0.82 mmol) at 0° C. The mixture was warmed to room temperature and continuously stirred at this temperature for 1.5 h. The reaction mixture was filtered through a short pad of Celite and concentrated in vacuo. The observed black solid was purified by flash column chromatography on silica gel using ethyl acetate and n-hexane (1:1, v/v) as the eluent to give 0.346 g g of a white solid 1a in 99% yield: R$_f$=0.13 (ethyl acetate:n-hexane=1:1 (v/v)); FT-IR (neat) ν$_{max}$ 3371, 3064, 2931, 2853, 1724, 1548, 1445, 1367, 1273, 1111, 1027, 892, 752, 712 cm$^{-1}$; $^1$H NMR (400 MHz, CDCl$_3$) δ 8.81-8.79 (m, 1H), 8.79-8.77 (m, 1H), 8.19-8.16 (m, 1H), 8.16-8.13 (m, 1H), 8.03-7.82 (m, 8H), 7.63-7.61 (m, 2H), 7.55-7.44 (m, 7H), 7.41-7.35 (m, 7H), 7.27-7.24 (m, 4H), 7.14-7.10 (m, 1H), 6.06 (t, J=2.2 Hz, 1H), 5.94-5.88 (m, 2H), 5.78-5.71 (m, 1H), 5.70 (d, J=9.9 Hz, 1H), 5.61 (dt, J=8.4, 2.2 Hz, 1H), 5.53 (d, J=9.5 Hz, 1H), 5.32-5.25 (m, 1H), 5.07 (dd, J=10.9, 2.9 Hz, 1H), 5.01 (dd, J=12.2, 2.2 Hz, 1H), 4.95 (dd, J=12.2, 2.2 Hz, 1H), 4.68 (dd, J=12.3, 5.8 Hz, 1H), 4.54 (dd, J=12.3, 8.6 Hz, 1H), 4.39 (q, J=10.2 Hz, 1H), 4.34 (dd, J=10.2, 2.2 Hz, 1H), 4.14 (q, J=10.2 Hz, 1H), 3.62 (s, 3H), 3.67 (s, 3H), 3.09 (dd, J=12.8, 4.7 Hz, 1H), 2.95 (dd, J=13.8, 4.7 Hz, 1H), 2.34 (dd, J=13.8, 11.5 Hz, 1H), 2.13 (dd, J=12.8, 11.5 Hz, 1H), 1.80 (s, 3H), 1.78 (s, 3H); $^{13}$C NMR (75 MHz, CDCl$_3$) 170.5 (C), 68.6 (C), 168.4 (C), 166.6 (C), 166.3 (C), 166.2 (C), 166.2 (C), 165.8 (C), 165.6 (C), 163.9 (C), 163.9 (C), 150.0 (CH), 147.4 (C), 147.3 (C), 137.1 (CH), 136.7 (CH), 136.2 (CH), 133.4 (CH), 133.3 (CH), 133.0 (CH), 132.9 (CH), 129.8 (CH), 129.7 (CH), 129.6 (CH), 129.5 (CH), 129.2 (CH), 129.1 (CH), 128.9 (CH), 128.8 (CH), 128.7 (CH), 128.5 (CH), 128.4 (CH), 128.3 (CH), 128.2 (CH), 127.1 (CH), 125.5 (CH), 89.1 (C), 88.1 (C), 75.3 (CH), 73.7 (CH), 73.3 (CH), 71.4 (CH), 70.2 (CH), 63.5 (CH$_2$), 63.0 (CH$_2$), 52.7 (CH$_3$), 52.7 (CH$_3$), 49.8 (CH), 48.9 (CH), 38.4 (CH$_2$), 38.0 (CH$_2$), 33.8 (CH$_2$), 23.0 (CH$_3$); HRMS-ESI [M+Na]$^+$ Calcd for C$_{45}$H$_{40}$N$_2$O$_{12}$SNa 855.2194, Found 855.2194.

1.1.3 Preparation of the Sialyl Donor 1d, 1f and 1g

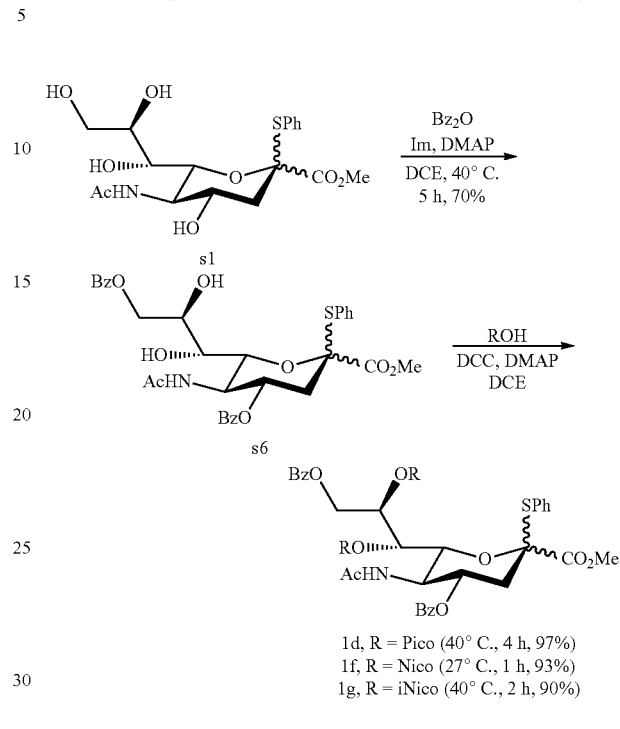

1d, R = Pico (40° C., 4 h, 97%)
1f, R = Nico (27° C., 1 h, 93%)
1g, R = iNico (40° C., 2 h, 90%)

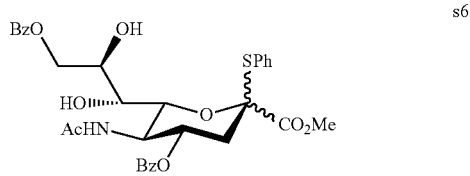

s6

Methyl (phenyl 5-acetamido-4,9-di-O-benzoyl-3,5-dideoxy-2-thio-D-glycero-D-galacto-non-2-ulopyranoside)onate (s6)

To a stirring solution of compound s1 (5.030 g, 12.02 mmol), Im (4.096 g, 60.21 mmol), DMAP (0.732 g, 0.60 mmol) in dry dichloroethane (120 mL) was added benzoic anhydride (10.848 g, 48.12 mmol) at 0° C. The mixture was warmed to 40° C. and continuously stirred at this temperature for 5 h. The reaction mixture was quenched with 6N HCl at ice bath, extracted with ethyl acetate, washed with cold saturated aqueous K$_2$CO$_3$ and brine, dried over MgSO$_4$, and concentrated in vacuo. The resulting white solid residue was purified by flash column chromatography on silica gel using ethyl acetate and n-hexane (1:1, v/v) as the eluent to get 5.263 g of s6 as a white solid compound in 70% yield, and 1.147 g of a white solid compound s5 in 13% yield: R$_f$=0.13 (ethyl acetate:n-hexane=1:1 (v/v)); FT-IR (neat) ν$_{max}$ 3349, 3065, 2953, 1720, 1660, 1603, 1551, 1446, 1375, 1272, 1116, 1070, 1027, 754, 713 cm$^{-1}$; $^1$H NMR (400 MHz, CDCl$_3$) δ 8.09-8.00 (m, 4H), 7.61-7.53 (m, 3H), 7.50-7.39 (m, 4H), 7.32-7.28 (m, 4H), 6.42 (d, J=8.2 Hz, 1H), 6.29 (d, J=8.2 Hz, 1H), 5.76-5.69 (m, 1H), 5.27-5.20 (m, 1H), 4.74 (dd, J=11.4, 2.4 Hz, 1H), 4.63 (dd, J=11.4, 2.4

Hz, 1H), 4.57 (d, J=7.2 Hz, 1H), 4.53-4.52 (m, 1H), 4.50 (dd, J=6.4, 5.6 Hz, 1H), 4.28-4.20 (m, 2H), 4.18-4.13 (m, 2H), 3.72 (dd, J=8.7, 0.8 Hz, 1H), 3.61 (d, J=8.7 Hz, 1H), 3.53 (s, 3H), 3.51 (s, 3H), 3.00 (dd, J=12.9, 4.8 Hz, 1H), 2.87 (dd, J=13.7, 4.8 Hz, 1H), 2.36 (dd, J=13.7, 11.8 Hz, 1H), 1.95 (s, 3H), 1.92 (s, 3H); $^{13}$C NMR (75 MHz, CDCl$_3$) δ 173.2 (C), 172.8 (C), 169.5 (C), 168.4 (C), 167.2 (C), 167.1 (C), 166.9 (C), 137.0 (CH), 135.7 (CH), 133.8 (CH), 133.1 (CH), 130.1 (CH), 129.9 (CH), 129.7 (CH), 129.6 (CH), 129.6 (CH), 129.5 (CH), 129.0 (CH), 128.9 (CH), 128.8 (CH), 128.7 (CH), 128.6 (CH), 128.4 (CH), 128.3 (CH), 89.4 (C), 85.8 (C), 73.0 (CH), 69.5 (CH), 69.3 (CH), 69.2 (CH), 67.5 (CH$_2$), 52.9 (CH$_3$), 52.6 (CH$_3$), 51.5 (CH), 51.0 (CH), 38.1 (CH$_2$), 37.3 (CH$_2$), 23.2 (CH$_3$), 22.9 (CH$_3$); HRMS-ESI [M+Na]$^+$ Calcd for C$_{32}$H$_{33}$NO$_{10}$SNa 646.1717, Found 646.1708.

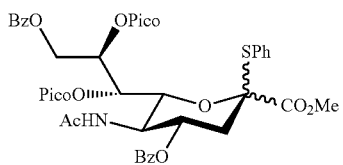

Methyl (phenyl 5-acetamido-4,9-di-O-benzoyl-3,5-dideoxy-7,8-di-O-picoloyl-2-thio-D-glycero-D-galacto-non-2-ulopyranoside)onate (1d)

To a stirring solution of compound s6 (3.790 g, 6.07 mmol) in dry dichloroethane (30 mL) was added 2-picolinic acid (1.867 g, 15.21 mmol), DMAP (0.074 g, 0.61 mmol) and DCC (3.754 g, 18.21 mmol) at 0° C. The mixture was warmed to 40° C. and continuously stirred at this temperature for 4 h. The reaction mixture was filtered through a short pad of Celite and concentrated in vacuo. The observed black solid was purified by flash column chromatography on silica gel using ethyl acetate as the eluent to give 4.938 g of a white solid 1d in 97% yield: R$_f$=0.30 (ethyl acetate); FT-IR (neat) ν$_{max}$ 3275, 3063, 1727, 1680, 1582, 1550, 1442, 1368, 1275, 1119, 1027, 996, 751, 712 cm$^{-1}$; $^1$H NMR (400 MHz, CDCl$_3$) δ 8.80-8.78 (m, 1H), 8.77-8.74 (m, 2H), 8.70-8.69 (m, 1H), 8.18 (d, J=7.8 Hz, 1H), 8.14 (d, J=7.8 Hz, 1H), 8.10 (d, J=7.8 Hz, 1H), 8.05 (d, J=7.8 Hz, 1H), 7.97-7.76 (m, 8H), 7.63-7.32 (m, 12H), 7.13-7.09 (m, 1H), 6.21 (d, J=9.7 Hz, 1H), 6.08 (t, J=2.4 Hz, 1H), 6.04 (dd, J=6.4, 1.3 Hz, 1H), 5.99-5.95 (m, 2H), 5.75-5.68 (m, 1H), 5.64 (dt, J=8.4, 2.2 Hz, 1H), 5.19-5.13 (m, 1H), 5.06-5.02 (m, 2H), 4.95 (dd, J=12.3, 2.4 Hz, 1H), 4.66 (dd, J=12.3, 6.0 Hz, 1H), 4.54 (dd, J=12.3, 8.4 Hz, 1H), 4.46 (q, J=10.1 Hz, 1H), 4.33-4.31 (m, 1H), 4.25 (q, J=10.1 Hz, 1H), 3.64 (s, 3H), 3.32 (s, 3H), 3.07 (dd, J=12.9, 4.8 Hz, 1H), 2.94 (dd, J=13.9, 4.8 Hz, 1H), 2.32 (dd, J=13.9, 11.8 Hz, 1H), 2.12 (dd, J=12.9, 11.8 Hz, 1H), 1.80 (s, 3H), 1.78 (s, 3H); $^{13}$C NMR (75 MHz, CDCl$_3$) δ 170.7 (C), 170.5 (C), 168.6 (C), 168.2 (C), 166.5 (C), 166.3 (C), 166.1 (C), 165.7 (C), 164.4 (C), 163.9 (C), 163.8 (C), 150.0 (CH), 149.9 (CH), 149.6 (CH), 147.5 (C), 147.1 (C), 137.5 (CH), 137.4 (CH), 137.0 (CH), 136.8 (CH), 136.1 (CH), 133.4 (CH), 132.9 (CH), 129.8 (CH), 129.8 (CH), 129.6 (CH), 129.5 (CH), 129.4 (CH), 129.1 (CH), 128.9 (CH), 128.6 (CH), 128.5 (CH), 128.2 (CH), 127.5 (CH), 127.3 (CH), 127.1 (CH), 126.9 (CH), 125.9 (CH), 125.6 (CH), 88.8 (C), 88.0 (C), 75.5 (CH), 74.8 (CH), 73.3 (CH), 72.7 (CH), 71.0 (CH), 70.6 (CH), 63.2 (CH$_2$), 62.8 (CH$_2$), 52.6 (CH$_3$), 52.6 (CH$_3$), 49.2 (CH), 49.0 (CH), 37.7 (CH$_2$), 23.1 (CH$_3$); HRMS-ESI [M+Na]$^+$ Calcd for C$_{44}$H$_{39}$N$_3$O$_{12}$SNa 856.2147, Found 856.2147.

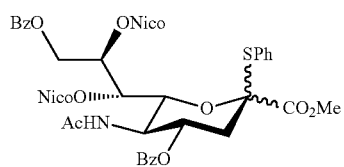

Methyl (phenyl 5-acetamido-4,9-di-O-benzoyl-3,5-dideoxy-7,8-di-O-nicotinoyl-2-thio-D-glycero-D-galacto-non-2-ulopyranoside)onate (1f)

To a stirring solution of compound s6 (0.500 g, 0.80 mmol) in dry dichloroethane (4.0 mL) was added nicotinic acid (0.246 g, 2.00 mmol), DMAP (0.010 g, 0.08 mmol) and DCC (0.380 g, 2.40 mmol) at 0° C. The mixture was warmed to 27° C. and continuously stirred at this temperature for 1 h. The reaction mixture was filtered through a short pad of Celite and concentrated in vacuo. The observed yellowish solid was purified by flash column chromatography on silica gel using ethyl acetate as the eluent to give 0.621 g of a white solid 1f in 93% yield: R$_f$=0.38 (ethyl acetate); FT-IR (neat) ν$_{max}$ 3269, 3062, 1728, 1684, 1591, 1543, 1475, 1446, 1369, 1272, 1201, 1109, 1026, 749, 712 cm$^{-1}$; $^1$H NMR (400 MHz, CDCl$_3$) δ 9.30 (dd, J=2.1, 0.7 Hz, 1H), 9.28 (dd, J=2.1, 0.7 Hz, 1H), 9.21 (dd, J=2.1, 0.7 Hz, 1H), 9.18 (dd, J=2.1, 0.7 Hz, 1H), 8.83-8.74 (m, 4H), 8.33-8.29 (m, 2H), 8.26-8.22 (m, 2H), 7.96-7.91 (m, 6H), 7.86-7.84 (m, 2H), 7.63-7.34 (m, 22H), 7.15-7.11 (m, 1H), 5.94 (t, J=2.0 Hz, 1H), 5.88-5.84 (m, 1H), 5.80 (dd, J=5.5, 0.7 Hz, 1H), 5.74-5.67 (m, 1H), 5.56 (d, J=10.0 Hz, 1H), 5.53 (dt, J=8.5, 2.0 Hz, 1H), 5.37-5.34 (m, 1H), 5.17-5.10 (m, 1H), 4.96-4.88 (m, 3H), 4.65 (dd, J=12.4, 6.3 Hz, 1H), 4.50 (dd, J=12.4, 8.6 Hz, 1H), 4.39 (q, J=10.3 Hz, 1H), 4.26-4.20 (m, 2H), 3.69 (s, 3H), 3.54 (s, 3H), 3.04 (dd, J=12.9, 4.7 Hz, 1H), 2.90 (dd, J=13.9, 4.9 Hz, 1H), 2.35 (dd, J=13.9, 11.7 Hz, 1H), 2.17 (dd, J=12.9, 11.7 Hz, 1H), 1.79 (s, 3H), 1.76 (s, 3H); $^{13}$C NMR (100 MHz, CDCl$_3$) δ 170.4 (C), 170.3 (C), 168.5 (C), 168.3 (C), 166.7 (C), 166.6 (C), 166.2 (C), 165.8 (C), 165.2 (C), 164.6 (C), 164.5 (C), 164.4 (C), 153.8 (CH), 151.3 (CH), 151.2 (CH), 151.2 (CH), 137.6 (CH), 137.5 (CH), 137.4 (CH), 137.4 (CH), 136.9 (CH), 136.2 (CH), 133.6 (CH), 133.6 (CH), 133.3 (CH), 133.1 (CH), 130.3 (CH), 130.0 (CH), 129.9 (CH), 129.9 (CH), 129.7 (C), 129.6 (CH), 129.6 (C), 129.5 (CH), 129.3 (CH), 129.1 (CH), 128.7 (CH), 128.7 (CH), 128.6 (C), 128.5 (CH), 128.5 (CH), 128.5 (CH), 128.4 (C), 126.0 (C), 125.7 (C), 125.7 (C), 123.6 (CH), 123.5 (CH), 89.0 (C), 87.7 (C), 75.8 (CH), 74.5 (CH), 73.7 (CH), 72.1 (CH), 70.7 (CH), 70.4 (CH), 69.9 (CH), 69.7 (CH), 63.0 (CH$_2$), 62.7 (CH$_2$), 53.0 (CH$_3$), 52.9 (CH$_3$), 49.9 (CH), 49.7 (CH), 38.5 (CH$_2$), 38.0 (CH$_2$), 23.2 (CH$_3$); HRMS-ESI [M+Na]$^+$ Calcd for C$_{44}$H$_{39}$N$_3$O$_{12}$SNa 856.2147, Found 856.2132.

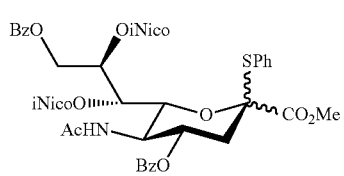

Methyl [phenyl 5-acetamido-4,9-di-O-benzoyl-3,5-dideoxy-7,8-di-O-isonicotinoyl-2-thio-D-glycero-D-galacto-non-2-ulopyranoside]onate (1g)

To a stirring solution of compound s6 (0.501 g, 0.80 mmol) in dry dichloroethane (4.0 mL) was added isonicotinic acid (0.246 g, 2.00 mmol), DMAP (0.010 g, 0.08 mmol) and DCC (0.380 g, 2.40 mmol) at 0° C. The mixture was warmed to 40° C. and continuously stirred at this temperature for 2 h. The reaction mixture was filtered through a short pad of Celite and concentrated in vacuo. The observed yellowish solid was purified by flash column chromatography on silica gel using ethyl acetate as the eluent to give 0.601 g of a white solid 1g in 90% yield: $R_f$=0.33 (ethyl acetate); FT-IR (neat) $v_{max}$ 3374, 3061, 1728, 1684, 1601, 1560, 1446, 1409, 1369, 1271, 1211, 1113, 1067, 1027, 997, 755, 712 cm$^{-1}$; $^1$H NMR (400 MHz, CDCl$_3$) δ 8.83-8.74 (m, 8H), 7.95-7.91 (m, 6H), 7.86-7.83 (m, 6H), 7.79-7.78 (m, 4H), 7.63-7.60 (m, 2H), 7.56-7.52 (m, 6H), 7.41-7.28 (m, 12H), 7.18-7.14 (m, 1H), 5.92 (t, J=2.0 Hz, 1H), 5.87-5.84 (m, 1H), 5.77 (dd, J=5.5, 0.7 Hz, 1H), 5.73-5.66 (m, 1H), 5.54 (d, J=10.0 Hz, 1H), 5.49 (dt, J=8.4, 2.1 Hz, 1H), 5.37 (d, J=8.2 Hz, 1H), 5.16-5.10 (m, 1H), 4.95-4.88 (m, 3H), 4.64 (dd, J=12.6, 6.3 Hz, 1H), 4.52 (dd, J=12.6, 8.4 Hz, 1H), 4.37 (q, J=10.2 Hz, 1H), 4.21-4.17 (m, 2H), 3.70 (s, 3H), 3.55 (s, 3H), 3.05 (dd, J=12.9, 4.7 Hz, 1H), 2.93 (dd, J=13.9, 4.8 Hz, 1H), 2.34 (dd, J=13.9, 11.6 Hz, 1H), 2.19 (dd, J=12.9, 12.0 Hz, 1H), 1.79 (s, 3H), 1.76 (s, 3H); $^{13}$C NMR (100 MHz, CDCl$_3$) δ 170.4 (C), 168.4 (C), 168.4 (C), 168.2 (C), 166.7 (C), 166.7 (C), 166.2 (C), 165.8 (C), 165.0 (C), 164.5 (C), 164.4 (C), 164.3 (C), 150.8 (CH), 150.7 (CH), 150.5 (CH), 137.3 (C), 137.0 (CH), 136.9 (C), 136.1 (CH), 133.7 (CH), 133.4 (CH), 133.2 (CH), 130.3 (CH), 130.1 (CH), 129.9 (CH), 129.7 (CH), 129.6 (CH), 129.4 (CH), 129.1 (CH), 129.1 (CH), 128.7 (CH), 128.5 (CH), 128.4 (CH), 123.2 (CH), 123.1 (CH), 123.1 (CH), 89.0 (C), 88.9 (C), 87.7 (C), 75.7 (CH), 74.7 (CH), 73.7 (CH), 72.2 (CH), 71.0 (CH), 70.3 (CH), 69.9 (CH), 69.8 (CH), 62.8 (CH$_2$), 62.5 (CH$_2$), 52.9 (CH$_3$), 49.9 (CH), 49.7 (CH), 38.6 (CH$_2$), 38.0 (CH$_2$), 23.2 (CH$_3$); HRMS-ESI [M+Na]$^+$ Calcd for C$_{44}$H$_{39}$NO$_{12}$SNa 856.2147, Found 856.2153.

1.1.4 Preparation of the Sialyl Donor 1d and 1b

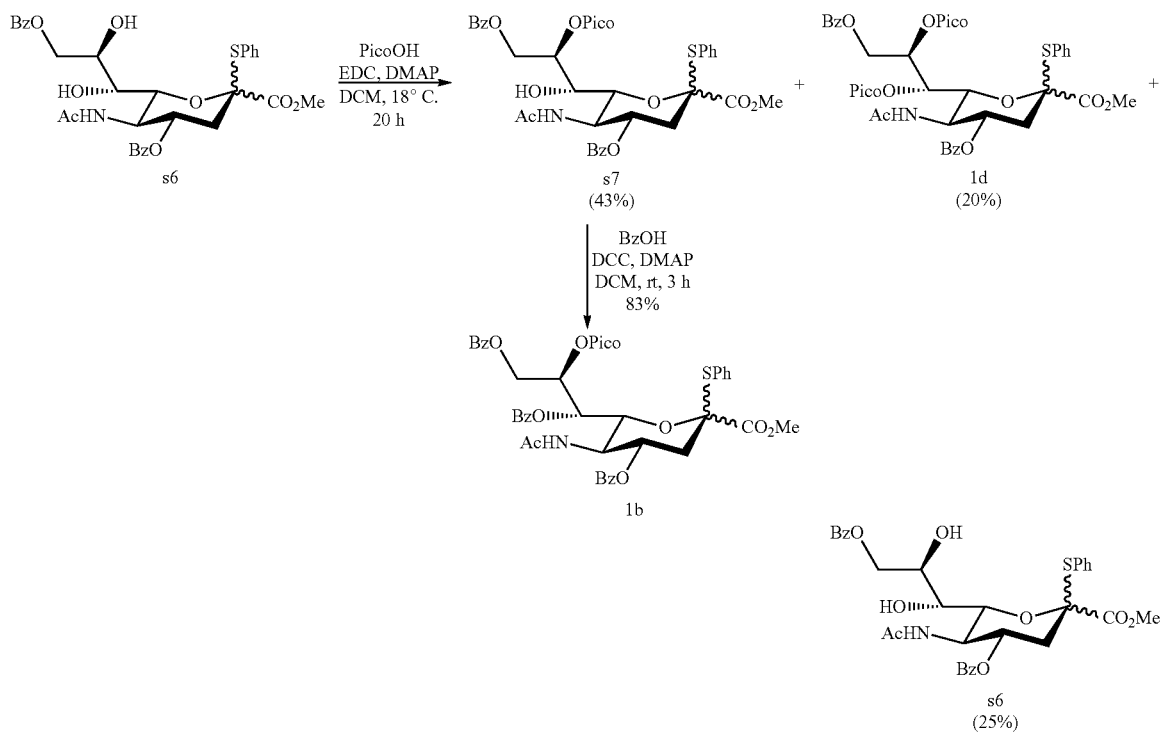

Methyl (phenyl 5-acetamido-4,9-di-O-benzoyl-3,5-dideoxy-8-O-picoloyl-2-thio-D-glycero-D-galacto-non-2-ulopyranoside)onate (s7)

To a stirring solution of compound s6 (0.450 g, 0.72 mmol) in dry CH$_2$Cl$_2$ (3.6 mL) was added 2-picolinic acid (0.151 g, 1.22 mmol), DMAP (0.088 g, 0.07 mmol) and EDC (0.276 g, 1.44 mmol) at 0° C. The mixture was warmed to 18° C. and continuously stirred at this temperature for 20 h. The reaction mixture was washed with brine, dried over MgSO$_4$, and concentrated in vacuo. The observed black solid residue was purified by flash column chromatography on silica gel using ethyl acetate and n-hexane (3:1, v/v) then ethyl acetate as the eluent to give 0.113 g of a white solid s6 in 25% yield, and 0.226 g of a white solid compound s7 in 43% yield, and 0.120 g of a white solid compound 1d in 20% yield: $R_f$=0.20 (ethyl acetate:n-hexane=3:1 (v/v)); FT-IR (neat) $v_{max}$ 3288, 3065, 1726, 1662, 1582, 1539, 1446, 1375, 1263, 1176, 1108, 1069, 1025, 754, 713 cm$^{-1}$; $^1$H NMR (400 MHz, CDCl$_3$) δ 8.72 (d, J=2.7 Hz, 1H), 8.16 (d, J=7.8 Hz, 1H), 8.01 (dd, J=8.4, 1.3 Hz, 2H), 7.90 (dd, J=8.4, 1.3 Hz, 2H), 7.80 (td, J=7.7, 1.7 Hz, 1H), 7.60 (t, J=7.4 Hz, 1H), 7.53-7.35 (m, 8H), 7.18 (t, J=7.6 Hz, 2H), 7.02 (t, J=7.4 Hz, 1H), 6.85-6.80 (m, 1H), 5.78-5.72 (m, 1H), 5.54 (dt, J=8.3, 2.5 Hz, 1H), 4.96 (dd, J=12.3, 2.0 Hz, 1H), 4.55 (d, J=10.2 Hz, 1H), 4.28-4.18 (m, 2H), 3.57 (s, 3H), 2.85 (dd, J=13.8, 4.8 Hz, 1H), 2.35 (dd, J=13.8, 11.6 Hz, 1H), 1.94 (s, 3H); $^{13}$C NMR (75 MHz, CDCl$_3$) δ 173.3 (C), 168.7 (C), 167.0 (C), 165.9 (C), 164.6 (C), 150.1 (CH), 149.9 (CH), 149.6 (CH), 147.7 (C), 146.8 (C), 137.3 (CH), 137.2 (CH), 137.1 (CH), 136.5 (CH), 136.1 (CH), 133.9 (CH), 133.6 (CH), 133.5 (CH), 133.1 (CH), 132.9 (CH), 132.8 (CH), 130.3 (C), 129.9 (CH), 129.8 (CH), 129.6 (CH), 129.1 (CH), 128.9 (CH), 128.8 (CH), 128.7 (CH), 128.4 (CH), 127.3 (CH), 127.2 (CH), 127.0 (CH), 125.7 (CH), 125.6 (CH), 89.2 (C), 87.8 (C), 76.2 (CH), 75.4 (CH), 74.7 (CH), 74.4 (CH), 72.4 (CH), 72.1 (CH), 70.3 (CH), 70.0 (CH), 69.7 (CH), 69.3 (CH), 67.7 (CH), 65.2 (CH), 64.0 (CH$_2$), 63.2 (CH$_2$), 52.7 (CH$_3$), 52.3 (CH$_3$), 51.7 (CH), 51.5 (CH), 37.8 (CH$_2$), 23.1 (CH$_3$); HRMS-ESI [M+Na]$^+$ Calcd for C$_{38}$H$_{36}$N$_2$O$_{11}$SNa 751.1932, Found 751.1937.

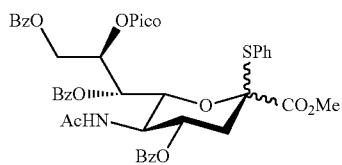

1b

Methyl (phenyl 5-acetamido-4,7,9-tri-O-benzoyl-3, 5-dideoxy-8-O-picoloyl-2-thio-D-glycero-D-galacto-non-2-ulopyranoside)onate (1b)

To a stirring solution of compound s7 (0.150 g, 0.21 mmol) in dry CH$_2$Cl$_2$ (2.0 mL) was added benzoic acid (0.038 g, 0.32 mmol), DMAP (0.003 g, 20.58 μmol) and DCC (0.085 g, 0.42 mmol) at 0° C. The mixture was warmed to 40° C. and continuously stirred at this temperature for 2 h. The reaction mixture was filtered through a short pad of Celite and concentrated in vacuo. The observed a white solid was purified by flash column chromatography on silica gel using ethyl acetate and CH$_2$Cl$_2$ (1:2, v/v) as the eluent to give 0.145 g of a white solid 1b in 83% yield: $R_f$=0.45 (ethyl acetate:CH$_2$Cl$_2$=1:1 (v/v)); FT-IR (neat) $v_{max}$ 3311, 3066, 3011, 2922, 2852, 1729, 1682, 1547, 1444, 1368, 1272, 1109, 1032, 892, 755, 713, 609 cm$^{-1}$; $^1$H NMR (400 MHz, CDCl$_3$) δ 8.80 (d, J=4.8 Hz, 1H), 8.77 (d, J=4.1 Hz, 1H), 8.18 (d, J=7.5 Hz, 1H), 8.16 (d, J=8.1 Hz, 1H), 8.07-7.93 (m, 10H), 7.88-7.86 (m, 3H), 7.79 (td, J=7.8, 1.5 Hz, 1H), 7.63-7.23 (m, 19H), 7.11 (t, J=7.4 Hz, 1H), 6.29 (d, J=8.7 Hz, 1H), 6.08-6.07 (m, 1H), 6.02-6.01 (m, 1H), 5.96-5.90 (m, 2H), 5.79-5.68 (m, 2H), 5.60-5.58 (m, 1H), 5.30-5.24 (m, 1H), 5.02-4.95 (m, 1H), 4.68 (dd, J=12.3, 6.2 Hz, 1H), 4.52 (dd, J=12.3, 8.7 Hz, 1H), 4.42 (q, J=10.2 Hz, 1H), 4.34-4.32 (m, 1H), 4.16 (q, J=10.6 Hz, 1H), 3.63 (s, 3H), 3.36 (s, 3H), 3.09 (dd, J=12.5, 4.6 Hz, 1H), 2.94 (dd, J=13.8, 4.5 Hz, 1H), 2.31 (dd, J=13.8, 11.6 Hz, 1H), 2.13 (dd, J=12.5, 11.5 Hz, 1H), 1.82 (s, 3H), 1.79 (s, 3H); $^{13}$C NMR (100 MHz, CDCl$_3$) δ 170.5 (C), 168.6 (C), 166.6 (C), 165.8 (C), 165.5 (C), 164.4 (C), 150.0 (CH), 147.2 (C), 137.5 (CH), 136.0 (CH), 133.4 (CH), 133.2 (CH), 132.9 (CH), 129.9 (CH), 129.9 (CH), 129.8 (C), 129.7 (CH), 129.5 (CH), 129.4 (CH), 129.0 (CH), 128.7 (C), 128.6 (CH), 128.5 (CH), 128.3 (CH), 128.2 (CH), 127.5 (CH), 125.8 (CH), 88.6 (C), 75.1 (CH), 73.2 (CH), 70.8 (CH), 70.0 (CH), 63.2 (CH$_2$), 52.7 (CH$_3$), 49.2 (CH), 37.7 (CH$_2$), 23.2 (CH$_3$); HRMS-ESI [M+Na]$^+$ Calcd for C$_{45}$H$_{40}$N$_2$O$_{12}$SNa 855.2194, Found 855.2181.

1.1.5 Preparation of the Sialyl Donor 1h

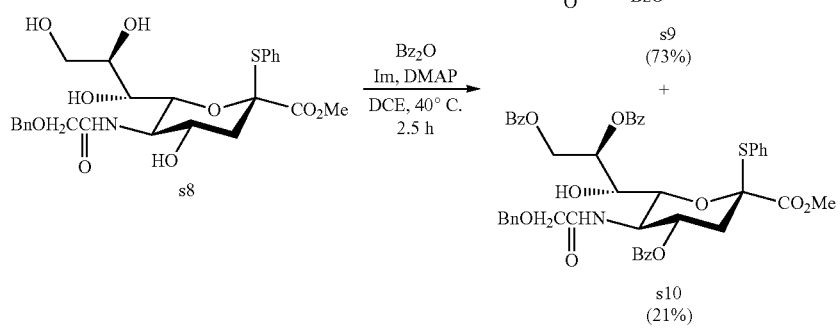

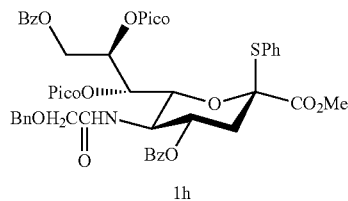

1h

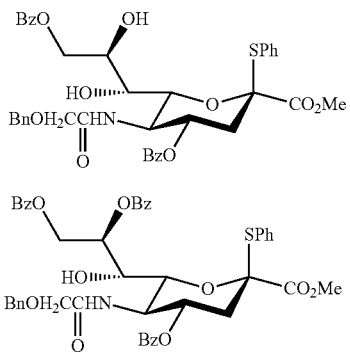

Methyl (phenyl 4,9-di-O-benzoyl-5-benzyloxyacet-amido-3,5-dideoxy-2-thio-D-glycero-D-galacto-non-2-ulopyranoside)onate (s9) and Methyl (phenyl 4,8,9-tri-O-benzoyl-5-benzyloxyacetamido-3,5-dideoxy-8-O-picoloyl-2-thio-D-glycero-D-galacto-non-2-ulopyranoside)onate (s10)

To a stirring solution of compound s8 (2.100 g, 4.02 mmol), Im (1.368 g, 20.11 mmol), DMAP (0.245 g, 2.01 mmol) in dry dichloroethane (40 mL) was added benzoic anhydride (3.637 g, 16.08 mmol) at 0° C. The mixture was warmed to 40° C. and continuously stirred at this temperature for 2.5 h. The reaction mixture was quenched with 6N HCl at ice bath, extracted with ethyl acetate, washed with cold saturated aqueous K$_2$CO$_3$ and brine, dried over MgSO$_4$, and concentrated in vacuo. The resulting white solid residue was purified by flash column chromatography on silica gel using ethyl acetate and n-hexane (1:1→3:1, v/v) as the eluent to get 2.143 g of s9 as a white solid compound in 73% yield, and 0.793 g of a white solid compound s10 in 21% yield: s9: R$_f$=0.13 (ethyl acetate:CH$_2$Cl$_2$=1:1 (v/v)); mp=99-100° C.; [α]$^{24}_D$ −28.7 (c 0.32, CHCl$_3$); FT-IR (neat) ν$_{max}$ 3343, 3064, 2951, 1719, 1665, 1602, 1534, 1447, 1375, 1313, 1273, 1117, 1070, 1026, 994, 895, 753, 713, 618 cm$^{-1}$; $^1$H NMR (400 MHz, CDCl$_3$) δ 8.06-8.00 (m, 4H), 7.62-7.59 (m, 3H), 7.50-7.43 (m, 4H), 7.33-7.29 (m, 6H), 7.25-7.23 (m, 2H), 7.16 (d, J=8.5 Hz, 1H), 5.85 (ddd, J=13.8, 8.7, 4.7 Hz, 1H), 4.72 (dd, J=11.8, 2.4 Hz, 1H), 4.57 (d, J=5.6 Hz, 1H), 4.52-4.44 (m, 4H), 4.31-4.23 (m, 1H), 4.15-4.11 (m, 1H), 3.91 (d, J=15.6 Hz, 1H), 3.82 (d, J=15.6 Hz, 1H), 3.64-3.62 (m, 1H), 3.57 (s, 3H), 2.89 (dd, J=13.8, 4.7 Hz, 1H), 2.44 (bs, 1H), 2.37 (dd, J=13.8, 11.8 Hz, 1H); $^{13}$C NMR (100 MHz, CDCl$_3$) δ 172.6 (C), 171.0 (C), 168.5 (C), 167.3 (C), 166.6 (C), 136.4 (C), 135.7 (CH), 133.7 (CH), 133.6 (CH), 133.1 (CH), 130.2 (CH), 130.1 (CH), 129.9 (CH), 129.7 (CH), 129.7 (CH), 129.5 (CH), 129.1 (CH), 129.0 (CH), 128.6 (CH), 128.5 (CH), 128.4 (CH), 128.3 (CH), 127.8 (CH), 89.1 (C), 73.5 (CH$_2$), 73.0 (CH), 69.4 (CH), 69.3 (CH), 68.9 (CH), 68.6 (CH$_2$), 67.5 (CH$_2$), 52.7 (CH$_3$), 51.2 (CH), 38.0 (CH$_2$); HRMS-ESI [M+Na]$^+$ Calcd for C$_{39}$H$_{39}$NO$_{11}$SNa 752.2136, Found 752.2118; s10: R$_f$=0.45 (ethyl acetate:CH$_2$Cl$_2$=1:1 (v/v)); mp=115-117° C.; [α]$^{24}_D$ −48.6 (c 0.15, CHCl$_3$); FT-IR (neat) ν$_{max}$ 3341, 3065, 1718, 1603, 1538, 1449, 1271, 1172, 1112, 1071, 1026, 890, 749, 711 cm$^{-1}$; $^1$H NMR (400 MHz, CDCl$_3$) δ 8.11-8.09 (m, 2H), 8.03-8.01 (m, 2H), 7.92-7.90 (m, 2H), 7.64-7.59 (m, 2H), 7.57-7.42 (m, 8H), 7.41-7.36 (m, 2H), 7.31-7.27 (m, 4H), 7.22-7.19 (m, 2H), 7.08-7.04 (m, 1H), 5.91-5.84 (m, 1H), 5.49 (ddd, J=8.0, 3.4, 2.0 Hz, 1H), 4.95 (dd, J=12.3, 2.0 Hz, 1H), 4.66 (dd, J=12.3, 8.0 Hz, 1H), 4.53-4.46 (m, 3H), 4.29 (d, J=10.3, 8.4 Hz, 1H), 4.07 (dd, J=3.4, 1.5 Hz, 1H), 3.96-3.83 (m, 2H), 3.56 (s, 3H), 2.88 (dd, J=13.8, 4.8 Hz, 1H), 2.40 (dd, J=13.8, 11.8 Hz, 1H); $^{13}$C NMR (75 MHz, CDCl$_3$) δ 173.1 (C), 171.0 (C), 168.7 (C), 166.6 (C), 166.4 (C), 166.0 (C), 136.5 (C), 136.2 (CH), 133.8 (CH), 133.6 (CH), 133.3 (CH), 132.9 (CH), 130.3 (CH), 130.2 (CH), 130.1 (CH), 130.0 (CH), 129.9 (CH), 129.8 (CH), 129.6 (CH), 129.1 (CH), 128.9 (CH), 128.7 (CH), 128.6 (CH), 128.5 (CH), 128.3 (CH), 128.2 (CH), 127.8 (CH), 89.4 (C), 74.5 (CH), 74.3 (CH), 73.5 (CH$_2$), 69.9 (CH), 68.9 (CH), 68.7 (CH$_2$), 64.1 (CH$_2$), 52.6 (CH$_3$), 51.1 (CH), 37.8 (CH$_2$); HRMS-ESI [M+Na]$^+$ Calcd for C$_{46}$H$_{43}$NO$_{12}$SNa 856.2398, Found 856.2419.

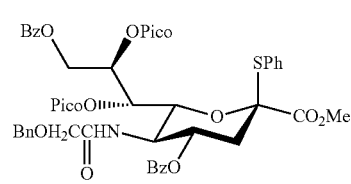

1h

Methyl (phenyl 4,9-di-O-benzoyl-5-benzyloxyacet-amido-3,5-dideoxy-7,8-di-O-picoloyl-2-thio-D-glycero-D-galacto-non-2-ulopyranoside)onate (1h)

To a stirring solution of compound s9 (1.795 g, 2.46 mmol) in dry dichloroethane (12 mL) was added 2-picolinic acid (0.758 g, 6.15 mmol), DMAP (0.030 g, 0.25 mmol) and DCC (1.524 g, 7.38 mmol) at 0° C. The mixture was warmed to 32° C. and continuously stirred at this temperature for 1 h. The reaction mixture was filtered through a short pad of Celite and concentrated in vacuo. The observed a yellowish solid was purified by flash column chromatography on silica gel using ethyl acetate and n-hexane (3:1→6:1, v/v) as the eluent to give 2.126 g of a white solid 1b in 92% yield: R$_f$=0.20 (ethyl acetate:CH$_2$Cl$_2$=4:1 (v/v)); mp=139-140° C.; [α]$^{24}_D$ +52.7 (c 0.15, CHCl$_3$); FT-IR (neat) ν$_{max}$ 3359, 3063, 3008, 2956, 1726, 1685, 1602, 1585, 1527, 1452, 1439, 1275, 1118, 1027, 994, 893, 751, 712, 619 cm$^{-1}$; $^1$H NMR (400 MHz, CDCl$_3$) δ 8.78-8.75 (m, 2H), 8.15 (dt, J=7.9, 1.0

Hz, 1H), 8.04 (dt, J=7.9, 1.0 Hz, 1H), 7.95-7.92 (m, 2H), 7.87-7.83 (m, 3H), 7.77 (td, J=7.9, 1.8 Hz, 1H), 7.56-7.50 (m, 4H), 7.49-7.42 (m, 2H), 7.39-7.28 (m, 7H), 7.21-7.18 (m, 2H), 7.14-7.10 (m, 1H), 6.81 (d, J=10.3 Hz, 1H), 6.03 (t, J=2.3 Hz, 1H), 5.71 (ddd, J=11.4, 10.0, 4.8 Hz, 1H), 5.66 (dt, J=8.4, 2.3 Hz, 1H), 5.04 (dd, J=10.9, 2.5 Hz, 1H), 4.95 (dd, J=12.3, 2.5 Hz, 1H), 4.54-4.49 (m, 3H), 4.45 (q, J=10.0 Hz, 1H), 3.90-3.64 (m, 5H), 2.97 (dd, J=13.9, 4.8 Hz, 1H), 2.32 (dd, J=13.9, 11.4 Hz, 1H); $^{13}$C NMR (75 MHz, CDCl$_3$) δ 170.5 (C), 168.5 (C), 166.1 (C), 165.7 (C), 164.3 (C), 164.0 (C), 150.1 (CH), 150.0 (CH), 147.6 (C), 147.3 (C), 137.2 (CH), 136.9 (CH), 136.9 (CH), 136.1 (CH), 133.3 (CH), 132.8 (CH), 129.8 (CH), 129.8 (CH), 129.5 (CH), 129.3 (CH), 129.2 (CH), 128.5 (CH), 128.3 (CH), 128.2 (CH), 127.7 (CH), 127.7 (CH), 127.6 (CH), 127.2 (CH), 126.9 (CH), 125.7 (CH), 125.5 (CH), 88.8 (C), 74.4 (CH), 73.2 (CH), 73.2 (CH$_2$), 71.3 (CH), 70.1 (CH), 69.3 (CH$_2$), 63.5 (CH$_2$), 52.6 (CH$_3$), 48.9 (C), 37.8 (CH$_2$); HRMS-ESI [M+Na]$^+$ Calcd for C$_{51}$H$_{45}$N$_3$O$_{13}$SNa 962.2565, Found 962.2550.

1.2 Coupling the Sialyl Donor of Example 1 with a Glucosyl Acceptor

In this example, the sialyl donor of example 1 (i.e., compounds 1a-e) were respectively coupled with a glucosyl acceptor 2 in accordance with the general condition described bellowed, and the product (i.e., compounds 3a-e and 4a-e) were isolated and analyzed by $^1$H-NMR. Results are summarized in Table 1.

General Procedures for Glycosylation:

A mixture of the sialyl donor of example 1 (1.0 equiv.), and acceptor (1.2 equiv.), and activated 3 Å powdered molecular sieves (1.0 g/mmol) in anhydrous CH$_2$Cl$_2$ (0.05 M) was stirred at room temperature for 1 h under nitrogen to remove any trace amounts of water. The reaction mixture was then cooled to −40° C. followed by addition of N-iodosuccinimide (NIS) (2 equiv.) and TfOH (1.5 equiv.). Continuously stirred at this temperature until thin-layer liquid chromatography (TLC) showed the reaction was completed, the reaction mixture was carefully quenched with triethylamine and then filtered through a short pad of Celite. The filtrate was washed with cold saturated aqueous Na$_2$S$_2$O$_3$, and brine, dried over MgSO$_4$, filtered, and concentrated in vacuo.

Disaccharide 3a and Glycal 4a

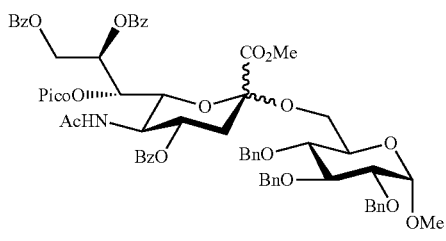

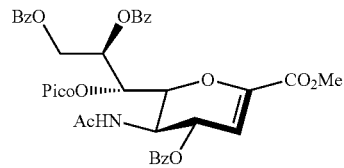

Methyl 5-acetamido-4,8,9-tri-O-benzoyl-3,5-dideoxy-7-O-picoloyl-D-glycero-D-galacto-non-2-ulopyranosylonate-(2→6)-methyl 2,3,4-tri-O-benzyl-α-D-glucopyranoside (3a) and methyl 5-acetamido-2,6-anhydro-4,8,9-tri-O-benzoyl-3,5-dideoxy-7-O-picoloyl-D-glycero-D-galacto-non-2-enonate (4a)

Treatment of thiosialoside 1a (0.304 g, 0.36 mmol), glucopyranoside acceptor 2 (0.201 g, 0.43 mmol) and activated 3 Å powdered molecular sieves (0.360 g) with CH$_2$Cl$_2$ (7.0 mL) in the presence of NIS (0.162 g, 0.72 mmol) and TfOH (0.048 g, 0.54 mmol) was according to the general procedure in 2 h. The produced yellowish syrup residue were purified by flash column chromatography on silica gel using ethyl acetate and CH$_2$Cl$_2$ (1:2, v/v) as the eluent to give to produce 0.243 g of colorless syrup disaccharide 3a in 57% yield, and 0.104 g of colorless syrup glycal 4a in 40% yield: 3a: R$_f$=0.23 (ethyl acetate:CH$_2$Cl$_2$=1:2 (v/v)); FT-IR (neat) ν$_{max}$ 3064, 3031, 2934, 1723, 1685, 1602, 1452, 1364, 1312, 1278, 1214, 1165, 1114, 1025, 751, 713 cm$^{-1}$; $^1$H NMR (400 MHz, CDCl$_3$) δ 8.81-8.80 (m, 1H), 8.70-8.69 (m, 1H), 8.21 (td, J=4.3, 0.9 Hz, 1H), 8.18-8.16 (m, 1H), 8.00-7.85 (m, 8H), 7.66 (td, J=7.7, 1.7 Hz, 1H), 7.55-7.27 (m, 29H), 6.01 (t, J=1.5 Hz, 1H), 5.94 (td, J=5.6, 1.6 Hz, 1H), 5.89 (dd, J=8.3, 2.0 Hz, 1H), 5.58 (dd, J=12.3, 2.4 Hz, 1H), 5.55-5.48 (m, 1H), 5.42-5.38 (m, 1H), 5.26-5.20 (m, 1H), 5.02-4.63 (m, 11H), 4.53 (dd, J=10.9, 2.0 Hz, 1H), 4.40 (q, J=10.3 Hz, 1H), 4.32 (dd, J=10.3, 4.6 Hz, 1H), 4.09 (d, J=10.7 Hz, 1H), 4.05-3.99 (m, 1H), 3.95 (d, J=10.7 Hz, 1H), 3.77 (s, 3H), 3.72 (dd, J=9.5, 3.5 Hz, 1H), 3.67 (dd, J=10.9, 2.4 Hz, 1H), 3.61 (t, J=9.5 Hz, 1H), 3.53 (dd, J=9.9, 3.5 Hz, 1H), 3.38 (s, 3H), 3.31 (s, 3H), 2.85 (dd, J=12.7, 4.8 Hz, 1H), 2.76 (dd, J=12.9, 5.0 Hz, 1H), 2.08 (dd, J=12.9, 11.4 Hz, 1H), 1.79 (s, 3H), 1.77 (s, 3H); $^{13}$C NMR (100 MHz, CDCl$_3$) δ 170.2 (C), 167.4 (C), 166.4 (C), 166.2 (C), 166.0 (C), 165.9 (C), 164.0 (C), 150.1 (CH), 147.6 (C), 138.9 (C), 138.5 (C), 138.5 (C), 137.1 (CH), 133.3 (CH), 133.2 (CH), 133.0 (CH), 129.9 (CH), 129.7 (CH), 129.5 (CH), 129.4 (CH), 128.5 (CH), 128.4 (CH), 128.4 (CH), 128.4 (CH), 128.3 (CH), 128.3 (CH), 128.8 (CH), 128.0 (CH), 127.9 (CH), 127.9 (CH), 127.7 (CH), 127.7 (CH), 127.5 (CH), 127.0 (CH), 125.6 (CH), 98.3 (C), 97.9 (CH), 82.2 (CH), 80.3 (CH), 75.8 (CH$_2$), 75.2 (CH), 74.2 (CH), 73.2 (CH$_2$), 72.1 (CH), 71.4 (CH), 69.8 (CH), 69.2 (CH), 63.5 (CH$_2$), 62.4 (CH$_2$), 55.0 (CH), 52.8 (CH), 49.7 (CH), 38.0 (CH$_2$), 23.2 (CH$_3$); HRMS-ESI [M+Na]$^+$ Calcd for C$_{67}$H$_{66}$N$_2$O$_{18}$Na 1209.4203, Found 1209.4214; 4a: R$_f$=0.20 (ethyl acetate:CH$_2$Cl$_2$=1:2 (v/v)); [α]$^{24}$$_D$ −99.0 (c 0.45, CHCl$_3$); FT-IR (neat) ν$_{max}$ 3320, 3063, 3006, 2931, 2851, 1727, 1664, 1593, 1541, 1445, 1372, 1269, 1107, 1022, 756, 713 cm$^{-1}$; $^1$H NMR (400 MHz, CDCl$_3$) δ 8.74-8.71 (m, 1H), 8.13 (d, J=7.8 Hz, 1H), 8.01-7.96 (m, 6H), 7.82 (t, J=7.8 Hz, 1H), 7.59-7.30 (m, 10H), 6.33 (d, J=5.7 Hz, 1H), 6.23-6.20 (m, 2H), 6.09-6.06 (m, 1H), 5.54 (dd, J=5.7, 3.9 Hz, 1H), 5.30 (dd, J=12.4, 2.8 Hz, 1H), 4.86 (ddd, J=12.4, 8.6, 3.9 Hz, 1H), 4.76-4.70 (m, 2H), 3.80 (s, 3H), 1.87 (s, 3H); $^{13}$C NMR (100 MHz, CDCl$_3$) δ 170.1 (C), 166.2 (C), 166.1 (C), 165.4 (C), 163.8 (C), 161.8 (C), 150.0 (CH), 147.1 (C), 146.6 (C), 137.1 (CH), 133.5 (CH), 133.4 (CH), 133.0 (CH), 129.8 (CH), 129.8 (CH), 129.7 (CH), 129.6 (CH), 129.3 (CH), 128.5 (CH), 128.5 (CH), 128.3 (CH), 127.2 (CH), 125.6 (CH), 106.2 (CH), 74.3 (CH), 72.5 (CH), 70.3 (CH), 65.1 (CH), 63.2 (CH$_2$), 52.6 (CH$_3$), 45.2 (CH), 23.1 (CH$_3$); HRMS-ESI [M+Na]$^+$ Calcd for C$_{39}$H$_{34}$N$_2$O$_{12}$Na 745.2004, Found 745.2005.

Disaccharide 3b and Glycal 4b

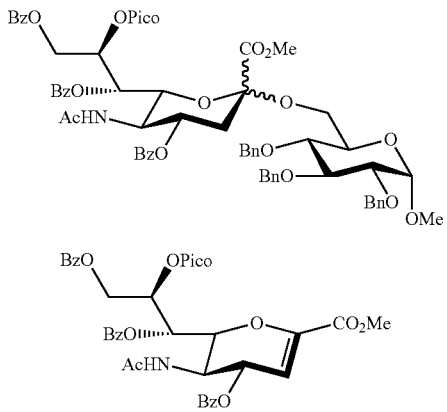

Methyl 5-acetamido-4,7,9-tri-O-benzoyl-3,5-dideoxy-8-O-picoloyl-D-glycero-D-galacto-non-2-ulopyranosylonate-(2→6)-methyl 2,3,4-tri-O-benzyl-α-D-glucopyranoside (3b) and methyl 5-acetamido-2,6-anhydro-4,7,9-tri-O-benzoyl-3,5-dideoxy-8-O-picoloyl-D-glycero-D-galacto-non-2-enonate (4b)

Treatment of thiosialoside 1b (0.050 g, 60.02 μmol), glucopyranoside acceptor 2 (0.033 g, 72.03 μmol) and activated 3 Å powdered molecular sieves (0.060 g) with $CH_2Cl_2$ (1.2 mL) in the presence of NIS (0.027 g, 0.12 mmol) and TfOH (0.008 mL, 90.03 mmol) was according to the general procedure in 2 h. The produced yellowish syrup residue were purified by flash column chromatography on silica gel using acetone and $Et_2O$ (1:6, v/v) as the eluent to give to produce 0.044 g of colorless syrup disaccharide 3b in 62% yield, and 0.010 g of colorless syrup glycal 4b in 24% yield: 3b: $R_f$=0.43 (acetone:n-hexane=1:1 (v/v)); FT-IR (neat) $v_{max}$ 3306, 2920, 2854, 1728, 1641, 1548, 1458, 1275, 1084, 751, 711 cm$^{-1}$; $^1$H NMR (400 MHz, CDCl$_3$) δ 8.76 (d, J=4.2 Hz, 1H), 8.07 (d, J=7.8 Hz, 1H), 7.97-7.90 (m, 6H), 7.80 (td, J=7.7, 1.5 Hz, 1H), 7.55-7.47 (m, 4H), 7.39-7.24 (m, 18H), 7.18-7.12 (m, 3H), 5.99-5.89 (m, 2H), 5.52 (d, J=9.7 Hz, 1H), 5.11-4.93 (m, 3H), 4.86-4.75 (m, 3H), 4.69-4.64 (m, 2H), 4.49-4.45 (m, 2H), 4.38 (dd, J=10.2, 3.7 Hz, 1H), 4.27 (q, J=10.2 Hz, 1H), 4.11 (dd, J=12.5, 6.2 Hz, 1H), 3.99 (t, J=9.2 Hz, 1H), 3.84-3.31 (m, 1H), 3.67 (t, J=9.4 Hz, 1H), 3.59 (dd, J=10.4, 1.7 Hz, 1H), 3.54 (dd, J=9.7, 3.4 Hz, 1H), 3.48 (s, 3H), 3.38 (s, 3H), 2.86 (dd, J=12.7, 4.5 Hz, 1H), 2.10 (t, J=12.7 Hz, 1H), 1.79 (s, 3H); $^{13}$C NMR (100 MHz, CDCl$_3$) δ 170.1 (C), 168.0 (C), 166.5 (C), 166.1 (C), 165.6 (C), 163.9 (C), 149.7 (CH), 148.2 (C), 139.1 (C), 138.5 (C), 138.4 (C), 137.1 (CH), 133.5 (CH), 133.4 (CH), 133.1 (CH), 130.0 (CH), 129.9 (CH), 129.9 (C), 129.6 (C), 129.4 (C), 128.6 (CH), 128.6 (CH), 128.5 (CH), 128.5 (CH), 128.4 (CH), 128.3 (CH), 128.1 (CH), 128.0 (CH), 127.7 (CH), 127.7 (CH), 127.0 (CH), 125.7 (CH), 125.7 (CH), 99.2 (C), 98.3 (CH), 82.2 (CH), 79.6 (CH), 75.9 (CH$_2$), 74.9 (CH$_2$), 73.5 (CH$_2$), 72.8 (CH), 70.1 (CH), 69.7 (CH), 69.7 (CH), 68.2 (CH), 63.7 (CH$_2$), 63.1 (CH$_2$), 55.3 (CH$_3$), 52.6 (CH$_3$), 49.8 (CH), 38.5 (CH$_2$), 30.5 (CH$_3$), 23.3 (CH$_3$); HRMS-ESI [M+Na]$^+$ Calcd for $C_{67}H_{66}N_2O_{18}Na$ 1209.4203, Found 1209.4181; 4b: $R_f$=0.38 (acetone:n-hexane=1:1 (v/v)); [α]$^{30}_D$+126.7 (c 0.20, CHCl$_3$); FT-IR (neat) $v_{max}$ 3277, 3066, 3016, 2960, 2925, 2855, 1729, 1671, 1593, 1546, 1445, 1368, 1262, 1104, 1029, 989, 908, 857, 755, 711, 610 cm$^{-1}$; $^1$H NMR (400 MHz, CDCl$_3$) δ 8.67 (d, J=4.4 Hz, 1H), 8.09 (d, J=7.4 Hz, 2H), 8.06 (d, J=7.9 Hz, 1H), 7.98 (t, J=6.4 Hz, 4H), 7.81 (t, J=7.7 Hz, 1H), 7.59 (t, J=7.4 Hz, 1H), 7.54-7.45 (m, 5H), 7.40-7.35 (m, 4H), 7.00 (bs, 1H), 6.17 (dd, J=5.0, 2.3 Hz, 1H), 6.09 (d, J=2.3 Hz, 1H), 6.07-6.04 (m, 1H), 5.93 (dd, J=8.8, 2.3 Hz, 1H), 5.25 (dd, J=12.4, 2.9 Hz, 1H), 4.94 (dd, J=10.7, 1.4 Hz, 1H), 4.72-4.60 (m, 2H), 3.77 (s, 3H), 1.84 (s, 3H); $^{13}$C NMR (100 MHz, CDCl$_3$) δ 170.4 (C), 166.6 (C), 166.3 (C), 165.7 (C), 164.1 (C), 161.9 (C), 149.9 (CH), 147.2 (C), 145.5 (C), 137.6 (CH), 133.5 (CH), 133.5 (CH), 133.2 (CH), 130.1 (CH), 130.0 (CH), 129.8 (CH), 129.6 (C), 129.5 (C), 128.7 (CH), 128.6 (CH), 128.5 (CH), 127.6 (CH), 125.9 (CH), 109.0 (CH), 76.9 (CH), 73.4 (CH), 70.2 (CH), 68.9 (CH), 63.0 (CH$_2$), 52.6 (CH$_3$), 47.2 (CH), 23.2 (CH$_3$); HRMS-ESI [M+Na]$^+$ Calcd for $C_{39}H_{34}N_2O_{12}Na$ 745.2004, Found 745.2005.

Disaccharide 3c and Glycal 4c

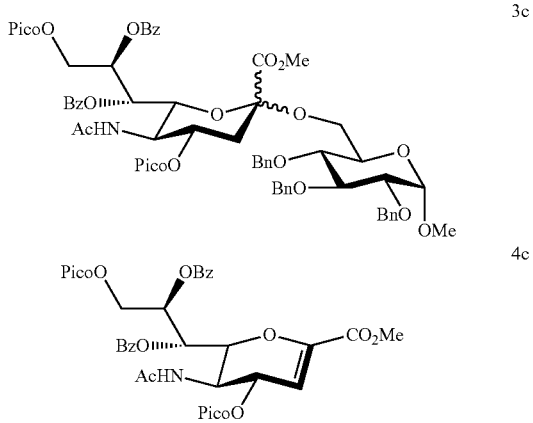

Methyl 5-acetamido-7,8-di-O-benzoyl-3,5-dideoxy-4,9-di-O-picoloyl-D-glycero-D-galacto-non-2-ulopyranosylonate-(2→6)-methyl 2,3,4-tri-O-benzyl-α-D-glucopyranoside (3c) and methyl 5-acetamido-2,6-anhydro-7,8-di-O-benzoyl-3,5-dideoxy-4,9-di-O-picoloyl-D-glycero-D-galacto-non-2-enonate (4c)

Treatment of thiosialoside 1c (0.080 g, 0.10 mmol), glucopyranoside acceptor 2 (0.060 g, 0.12 mmol) and activated 3 Å powdered molecular sieves (0.120 g) with $CH_2Cl_2$ (1.9 mL) in the presence of NIS (0.043 g, 0.19 mmol) and TfOH (0.013 mL, 0.14 mmol) was according to the general procedure in 2 h. The produced yellowish syrup residue were purified by flash column chromatography on silica gel using ethyl acetate then acetone/$CH_2Cl_2$ (1/1, v/v) as the eluent to give to produce 0.049 g of colorless syrup disaccharide 3c in 43% yield, and 0.034 g of colorless syrup glycal 4c in 43% yield: 3c: $R_f$=0.13 (ethyl acetate); FT-IR (neat) $v_{max}$ 3326, 2922. 2854, 1733, 1678, 1546, 1446, 1366, 1280, 1095, 752, 708, 613 cm$^{-1}$; $^1$H NMR (400 MHz, CDCl$_3$) δ 8.79 (d, J=4.3 Hz, 1H), 8.76 (d, J=4.9 Hz, 1H), 8.74 (d, J=4.7 Hz, 2H), 8.12 (dd, J=7.4 Hz, 2H), 8.06-7.93 (m, 12H), 7.81-7.77 (m, 4H), 7.70 (td, J=7.8, 1.5 Hz, 1H), 7.62-7.30 (m, 37H), 7.23-7.22 (m, 6H), 6.29 (dd, J=8.6, 7.6

Hz, 1H), 5.97-5.86 (m, 4H), 5.75-5.68 (m, 1H), 5.55 (dd, J=11.9, 3.7 Hz, 1H), 5.44-5.37 (m, 1H), 4.97-4.58 (m, 20H), 4.38 (dd, J=12.2, 5.8 Hz, 1H), 4.34 (q, J=10.0 Hz, 1H), 4.22 (q, J=9.8 Hz, 1H), 4.15 (dd, J=10.4, 4.5 Hz, 1H), 4.05 (d, J=10.5 Hz, 1H), 4.00-3.92 (m, 2H), 3.85 (d, J=11.0 Hz, 1H), 3.80-3.78 (m, 2H), 3.73-3.70 (m, 4H), 3.61-3.57 (m, 2H), 3.52-3.47 (m, 3H), 3.43 (s, 3H), 3.34 (s, 6H), 2.82 (dd, J=12.6, 4.9 Hz, 1H), 2.72 (dd, J=13.1, 5.0 Hz, 1H), 2.16-2.08 (m, 2H), 1.81 (s, 3H), 1.78 (s, 3H); $^{13}$C NMR (100 MHz, CDCl$_3$) δ 170.5 (C), 170.4 (C), 170.0 (C), 167.4 (C), 166.2 (C), 165.7 (C), 165.6 (C), 165.5 (C), 164.6 (C), 164.5 (C), 164.5 (C), 164.3 (C), 150.2 (CH), 150.1 (CH), 150.0 (CH), 147.6 (C), 147.5 (C), 147.4 (C), 147.2 (C), 139.0 (C), 138.8 (C), 138.6 (C), 138.6 (C), 138.4 (C), 138.3 (C), 137.4 (CH), 137.3 (CH), 137.2 (CH), 137.1 (CH), 133.3 (CH), 133.1 (CH), 130.0 (CH), 129.9 (CH), 129.8 (C), 129.7 (C), 129.5 (CH), 128.6 (CH), 128.5 (CH), 128.4 (CH), 128.4 (CH), 128.3 (CH), 128.2 (CH), 128.1 (CH), 128.0 (CH), 127.9 (CH), 127.8 (CH), 127.7 (CH), 127.7 (CH), 127.6 (CH), 127.3 (CH), 127.2 (CH), 125.7 (CH), 125.6 (CH), 125.4 (CH), 125.0 (CH), 99.1 (C), 98.2 (C), 98.1 (CH), 98.0 (CH), 82.3 (CH), 82.0 (CH), 80.1 (CH), 79.7 (CH), 77.6 (C), 77.4 (C), 75.8 (CH$_2$), 75.8 (CH$_2$), 75.2 (CH$_2$), 74.9 (CH$_2$), 73.9 (CH), 73.4 (CH$_2$), 73.2 (CH$_2$), 72.5 (CH), 71.5 (CH), 71.0 (CH), 70.8 (CH), 70.7 (CH), 69.6 (CH), 69.5 (CH), 69.4 (CH), 69.4 (CH), 64.0 (CH$_2$), 63.7 (CH$_2$), 63.6 (CH$_2$), 62.6 (CH$_2$), 55.2 (CH$_3$), 55.1 (CH$_3$), 52.8 (CH$_3$), 52.5 (CH$_3$), 50.1 (CH), 49.9 (CH), 38.3 (CH$_2$), 37.9 (CH$_2$), 23.2 (CH$_3$), 23.2 (CH$_3$); HRMS-ESI [M+Na]$^+$ Calcd for C$_{66}$H$_{65}$N$_3$O$_{18}$Na 1210.4155, Found 1210.4135; 4c: R$_f$ 0.13 (ethyl acetate); [α]$^{30}$$_D$ +162.8 (c 0.31, CHCl$_3$); FT-IR (neat) ν$_{max}$ 3318, 3064, 3006, 2923, 2853, 1732, 1673, 1578, 1545, 1444, 1369, 1254, 1100, 1035, 991, 907, 855, 755, 711, 614 cm$^{-1}$; $^1$H NMR (400 MHz, CDCl$_3$) δ 8.85 (d, J=4.0 Hz, 1H), 8.72 (d, J=4.3 Hz, 1H), 8.10 (d, J=8.0 Hz, 4H), 7.94 (d, J=8.0 Hz, 2H), 7.83 (td, J=8.0, 1.2 Hz, 1H), 7.78 (td, J=8.0, 1.2 Hz, 1H), 7.60 (t, J=7.5 Hz, 1H), 7.53-7.43 (m, 5H), 7.35 (t, J=7.7 Hz, 2H), 7.13 (d, J=9.3 Hz, 1H), 6.17 (dd, J=8.4, 2.5 Hz, 1H), 6.11 (t, J=3.4 Hz, 1H), 6.07 (d, J=2.6 Hz, 1H), 6.00-5.97 (m, 1H), 5.19 (dd, J=12.2, 3.4 Hz, 1H), 5.06 (dd, J=10.5, 2.8 Hz, 1H), 4.75 (dd, J=12.2, 5.9 Hz, 1H), 4.53 (q, J=9.5 Hz, 1H), 3.65 (s, 3H), 1.89 (s, 3H); $^{13}$C NMR (100 MHz, CDCl$_3$) δ 171.8 (C), 165.6 (C), 165.6 (C), 164.9 (C), 164.7 (C), 161.8 (C), 150.1 (CH), 150.0 (CH), 147.4 (C), 147.0 (C), 145.7 (C), 137.5 (CH), 137.3 (CH), 133.4 (CH), 133.3 (CH), 130.0 (CH), 129.8 (CH), 129.5 (C), 129.3 (C), 128.6 (CH), 128.4 (CH), 127.5 (CH), 127.3 (CH), 125.9 (CH), 125.4 (CH), 108.3 (CH), 76.6 (CH), 71.4 (CH), 71.2 (CH), 69.1 (CH), 64.2 (CH$_2$), 52.5 (CH$_3$), 47.0 (CH), 23.1 (CH$_3$); HRMS-ESI [M+Na]$^+$ Calcd for C$_{38}$H$_{33}$N$_3$O$_{12}$Na 746.1956, Found 746.1952.

Disaccharide 3d and Glycal 4d

3d

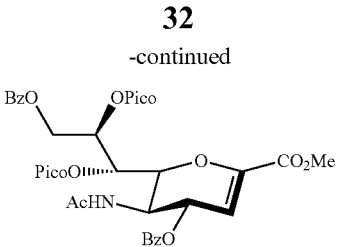

4d

Methyl 5-acetamido-4,9-di-O-benzoyl-3,5-dideoxy-7,8-di-O-picoloyl-D-glycero-α-D-galacto-non-2-ulopyranosylonate-(2→6)-methyl 2,3,4-tri-O-benzyl-α-D-glucopyranoside (3d) and methyl 5-acetamido-2,6-anhydro-4,9-di-O-benzoyl-3,5-dideoxy-7,8-di-O-picoloyl-D-glycero-D-galacto-non-2-enonate (4d)

Treatment of thiosialoside 1d (0.030 g, 35.97 μmol), glucopyranoside acceptor 2 (0.020 g, 43.16 μmol) and activated 3 Å powdered molecular sieves (0.040 g) with CH$_2$Cl$_2$ (0.7 mL) in the presence of NIS (0.016 g, 71.94 μmol) and TfOH (0.002 mL, 53.96 μmol) was according to the general procedure in 2 h. The produced yellowish syrup residue were purified by flash column chromatography on silica gel using ethyl acetate as the eluent to give to produce 0.030 g of a white solid disaccharide 3d in 70% yield, and 0.007 g of a white solid glycal 4d in 27% yield: 3d: R$_f$ 0.28 (ethyl acetate); mp=111-112° C.; [α]$^{24}$$_D$ +52.4 (c 0.35, CHCl$_3$); FT-IR (neat) ν$_{max}$ 3330, 3062, 3008, 2926, 1730, 1678, 1579, 1446, 1366, 1280, 1121, 752, 709 cm$^{-1}$; $^1$H NMR (400 MHz, CDCl$_3$) δ 8.73 (d, J=4.4 Hz, 1H), 8.66 (d, J=4.2 Hz, 1H), 8.06 (d, J=7.8 Hz, 1H), 7.98-7.90 (m, 5H), 7.79 (td, J=7.7, 1.6 Hz, 1H), 7.64 (td, J=7.7, 1.7 Hz, 1H), 7.54-7.46 (m, 3H), 7.42-7.29 (m, 16H), 7.26-7.11 (m, 4H), 6.01-5.95 (m, 2H), 5.66 (d, J=9.8 Hz, 1H), 5.12-5.05 (m, 1H), 5.03-4.64 (m, 7H), 4.60-4.57 (m, 1H), 4.49 (d, J=10.8 Hz, 1H), 4.37 (dd, J=10.6, 3.9 Hz, 1H), 4.29 (q, J=10.2 Hz, 1H), 4.07 (dd, J=12.5 Hz, 1H), 4.00 (t, J=9.2 Hz, 1H), 3.83-3.80 (m, 1H), 3.66 (t, J=9.4 Hz, 1H), 3.61 (dd, J=10.6, 1.7 Hz, 1H), 3.54 (dd, J=9.7, 3.4 Hz, 1H), 3.45 (s, 3H), 3.38 (s, 3H), 2.85 (dd, J=12.7, 4.6 Hz, 1H), 2.11 (t, J=12.7 Hz, 1H), 1.79 (s, 3H); $^{13}$C NMR (100 MHz, CDCl$_3$) δ 170.4 (C), 168.0 (C), 166.4 (C), 166.0 (C), 164.0 (C), 163.8 (C), 150.1 (CH), 149.5 (CH), 148.0 (C), 147.4 (C), 139.1 (C), 138.7 (C), 138.3 (C), 137.2 (CH), 136.9 (CH), 133.4 (CH), 133.0 (CH), 129.9 (CH), 129.9 (CH), 129.8 (C), 129.4 (C), 128.6 (CH), 128.5 (CH), 128.4 (CH), 128.4 (CH), 128.2 (CH), 128.0 (CH), 128.0 (C), 127.7 (CH), 127.6 (CH), 127.6 (CH), 127.1 (CH), 127.0 (CH), 125.7 (CH), 125.5 (CH), 99.1 (C), 98.2 (CH), 82.1 (CH), 79.6 (CH), 75.8 (CH$_2$), 74.8 (CH$_2$), 73.4 (CH$_2$), 72.6 (CH), 70.2 (CH), 69.7 (CH), 69.7 (CH), 68.8 (CH), 63.7 (CH$_2$), 62.6 (CH$_2$), 55.2 (CH$_3$), 52.5 (CH$_3$), 49.7 (CH), 38.5 (CH$_2$), 23.2 (CH$_3$); HRMS-ESI [M+Na]$^+$ Calcd for C$_{66}$H$_{65}$N$_3$O$_{18}$Na 1210.4155, Found 1210.4101.

Disaccharide 3e

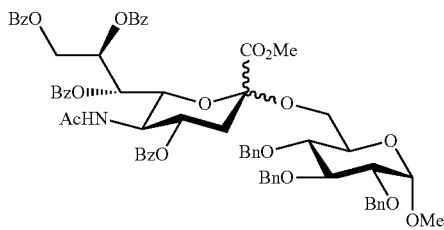

Methyl 5-acetamido-4,7,8,9-tetra-O-benzoyl-3,5-dideoxy-D-glycero-D-galacto-non-2-ulopyranosylonate-(2→6)-methyl 2,3,4-tri-O-benzyl-α-D-glucopyranoside (3e)

Treatment of thiosialoside 1e (0.300 g, 0.36 mmol), glucopyranoside acceptor 2 (0.201 g, 0.43 mmol) and activated 3 Å powdered molecular sieves (0.467 g) with $CH_2Cl_2$ (7.0 mL) in the presence of NIS (0.162 g, 0.72 mmol) and TfOH (0.048 g, 0.54 mmol) was according to the general procedure in 2 h. The produced yellowish syrup residue were purified by flash column chromatography on silica gel using ethyl acetate and n-hexane (1:2→1:1, v/v) as the eluent to give to produce 0.398 g of a white solid disaccharide 3e in 90% yield: $R_f$=0.25 (ethyl acetate:n-hexane=1:2 (v/v)); FT-IR (neat) $v_{max}$ 3395, 3065, 3031, 2935, 1724, 1602, 1527, 1452, 1364, 1315, 1270, 1215, 1171, 1100, 1071, 1025, 754, 713 cm$^{-1}$; $^1$H NMR (400 MHz, CDCl$_3$) δ 8.14-8.12 (m, 2H), 7.99-7.97 (m, 2H), 7.95-7.92 (m, 2H), 7.88-7.85 (m, 2H), 7.62-7.29 (m, 27H), 5.93 (t, J=1.7 Hz, 1H), 5.90-5.87 (m, 1H), 5.60-5.57 (m, 2H), 5.52-5.45 (m, 1H), 5.02-4.79 (m, 7H), 4.70-4.63 (m, 2H), 4.35 (q, J=10.2 Hz, 1H), 4.09-4.00 (m, 2H), 3.96-3.94 (m, 1H), 3.78 (s, 3H), 3.72 (dd, J=9.6, 3.6 Hz, 1H), 3.29 (s, 3H), 2.74 (dd, J=12.9, 5.0 Hz, 1H), 2.05 (dd, J=12.9, 11.9 Hz, 1H), 1.77 (s, 3H); $^{13}$C NMR (75 MHz, CDCl$_3$) δ 170.1 (C), 167.4 (C), 166.5 (C), 166.4 (C), 166.1 (C), 165.5 (C), 138.9 (C), 138.6 (C), 138.5 (C), 133.3 (CH), 133.3 (CH), 133.2 (CH), 133.0 (CH), 130.0 (CH), 129.9 (CH), 129.8 (CH), 129.8 (CH), 129.5 (CH), 128.6 (CH), 128.5 (CH), 128.4 (CH), 128.4 (CH), 128.3 (CH), 128.1 (CH), 128.0 (CH), 127.8 (CH), 127.7 (CH), 127.6 (CH), 98.3 (CH), 98.0 (CH), 82.2 (CH), 80.1 (CH), 75.8 (CH$_2$), 75.2 (CH$_2$), 74.8 (CH), 73.2 (CH$_2$), 72.2 (CH), 70.4 (CH), 69.9 (CH), 69.4 (CH), 63.5 (CH$_2$), 62.5 (CH$_2$), 55.0 (CH$_3$), 52.8 (CH$_3$), 49.6 (CH), 38.0 (CH$_2$), 23.2 (CH$_3$); HRMS-ESI [M+Na]$^+$ Calcd for C$_{68}$H$_{67}$NO$_{18}$Na 1208.4250, Found 1208.4226.

TABLE 1

The Glycosylation of Sialyl Donors 1a-e with Glucosyl Acceptor 2

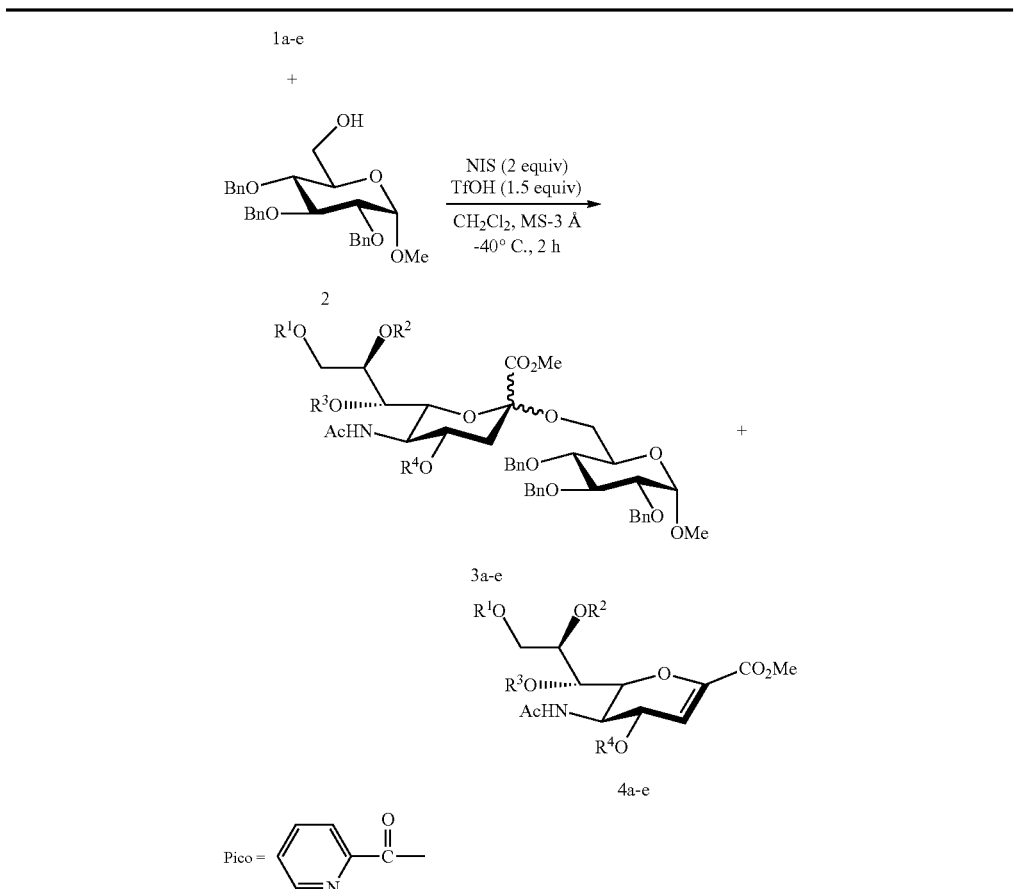

TABLE 1-continued

The Glycosylation of Sialyl Donors 1a-e with Glucosyl Acceptor 2

| entry | donor | Yield[a] of 3a-e (α/β)[b] | Yield[a] of 4a-e |
|---|---|---|---|
| 1 | 1a | 3a, 57% (α/β = 1:1.2) | 4a, 40% |
| 2 | 1b | 3b, 62% (α/β = 8:1) | 4b, 24% |
| 3 | 1c | 3c, 43% (α/β = 1.3:2) | 4c, 49% |
| 4 | 1d | 3d, 70% (α only) | 4d, 27% |
| 5 | 1e | 3e, 90% (α/β = 1:3.3) | 4e, 0% |

[a]Isolated through chromatography.
[b]It is determined by $^1$H NMR spectrum.

It was evident from the data presented in Table 1 that the best result was obtained with the glycosylation of sialyl donor 1d with the acceptor 2 at −40° C., in which the yield of the product 3d was about 70% with excellent stereoselectivity (α only) along with product 4d in 27% yield. The sialyl donor 1b also exhibited high high α-stereoselectivity (α/β=8:1) and moderate yield of disaccharide 3b (62%), with product 4b in 24% yield. Sialyl compounds 1a and 1c, by contrast, had no significant stereoselectivity for disaccharide 3a (α/β=1:1.2, 57% yield) and 3c (α/β=1.3:1, 43% yield), while compounds of 4a and 4c were about 40% and 49% yield, respectively. Sialyl donor 1e gave disaccharide 3e in excellent yield (90%), but with poor α-stereoselectivity (α/β=1:3.3) and moderate yield of disaccharide 3b (62%), with product 4b in 24% yield.

1.3 Screening for the Optimal Glycosylation Condition

To find out the optimal glycosylation condition for the coupling reaction of Example 1.2, the coupling of sialyl donor 1d and acceptor 2 was conducted in accordance with the similar procedures described in Example 1.2 except the solvent and temperature were varied, and the products 3d and 4d were then isolated and analyzed. Results are summarized in Table 2.

TABLE 2

Screening for optimal glycosylation condition for the glycosylation of sialyl donor 1d and acceptor 2

| Entry | Solvent | Temp (° C.) | Time (hr) | Yield (%)[a] of 3d ($\alpha/\beta$)[b] | Yield (%)[a] of 4d |
|---|---|---|---|---|---|
| 1 | $CH_2Cl_2$ | −20 | 0.5 | 24 (5.3:1) | 70 |
| 2 | $CH_2Cl_2$ | −60 | 5.0 | 69 ($\alpha$ only) | 25 |
| 3 | $CH_3CN$ | −40 | 0.5 | 56 ($\alpha$ only) | 44 |
| 4 | $CHCl_3$ | −40 | 0.5 | 20 ($\alpha$ only) | 76 |
| 5 | Toluene | −40 | 2.0 | —[c] | 0 |

[a]Isolated through chromatography.
[b]It is determined by $^1H$ NMR spectrum.
[c]The starting material was recovered.

As evident from the data presented in Table 2, when the coupling temperature was elevated from −40° C. to −20° C., it resulted in a decrease in the $\alpha$-stereoselectivity ($\alpha$-only vs $\alpha/\beta$=5.3:1) and the production yield (70% vs 24%). By contrast, if the coupling temperature was further decreased to −60° C., the yield (69%) and $\alpha$-stereoselectivity ($\alpha$-only) of the disaccharide 3d remained comparable to those at −40° C., except the reaction now took much longer time to complete, about 5 hrs.

If the coupling reaction was performed in $CH_3CN$ or $CHCl_3$ instead of $CH_2Cl_2$, the $\alpha$-stereoselectivity remained excellent ($\alpha$-only), yet the production yield of the disaccharide 3d was not satisfactory (56% or 20%). In the case when the solvent was switched to toluene, glycosylation failed to proceed at all.

Example 2 Screening for Glycosyl Acceptor of the Sialyl Donor of Example 1

In this example, various glycosyl acceptors were prepared and tested for its efficacy in conjugating with the sialyl donor 1d by use of the optimal condition identified in of Example 1.3. Representative results are summarized in Table 3.

TABLE 3

Screening for glycosyl acceptor of the sialyl donor of Example 1

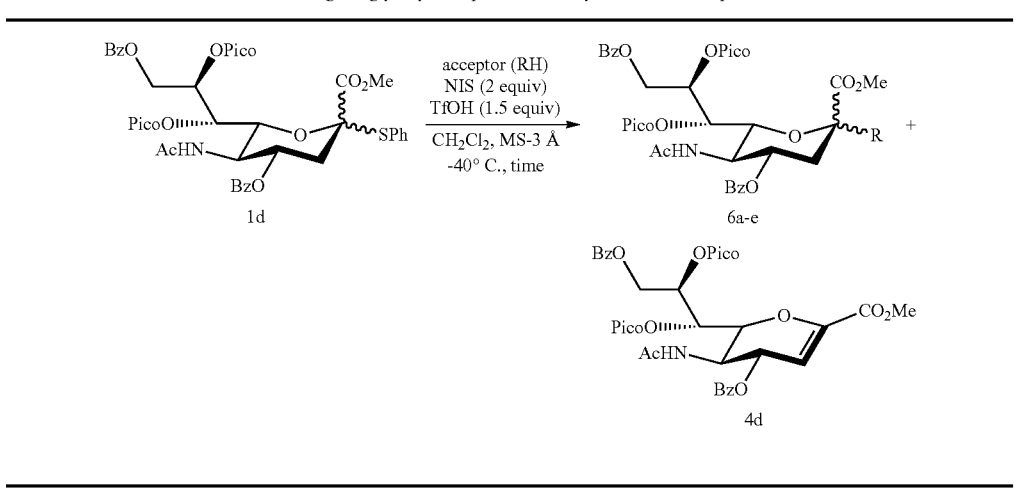

TABLE 3-continued

Screening for glycosyl acceptor of the sialyl donor of Example 1

| 3 | 5c | 0.5 | 6c, 68% (α only) | 25 |
| 4 | 5d | 0.5 | 6d, 73% (α only) | 20 |
| 5 | 5e | 1.0 | 6e, 0% | 99 |

[a]Isolated by chromatography.
[b]Determined by ¹H NMR spectroscopy.

It is evident form the data presented in Table 3 that the glycoconjugation of sialyl donor 1d and the primary alcohol 5a gave rise to the highest production yield (97%) of dissacharide 6a as a single α-stereoisomer. The primary alcohol 5b also gave excellent production yield of 98%, however, the α-stereoselectivity was not satisfactory (α/β=2.8:1). The other two primary alcohols 5c and 5d gave moderate yields of dissacharides 6c and 6d (68% and 73%, respectively) with excellent α-stereoselectivity (α only). In the case when a primary sugar 5e was used as an acceptor, no corresponding dissacharide 6e was found, but the glycal side product 4d (99%).

Example 3 Synthesis of Hp-s1 Using the Sialyl Donor and the Optimal Glycosylation Condition Identified in Example 1

To confirm the utility of the present disclosure, the methodology and the sialyl donor identified Example 1 were applied to the synthesis of a natural ganglioside, Hp-s1 in accordance with the procedures set forth in Scheme I. In general, the sialylation of S-thiazolyl (STaz) acceptor 8 with the sialyl donor 1d was conducted at the optimal condition identified in Example 1, in which NIS/TfOH were used as promotors, and the coupling reaction was performed in $CH_2Cl_2$ with the addition of powdered 3 Å molecule sieve (MS-3 Å) at −40° C. The coupling gave rise to the α-stereoisomer disaccharide 9 (76% yield), which was then coupled with protected photoceramide 11 in the presence of a promoter (e.g., AgOTf) in anhydrous $CH_2Cl_2$ at 0° C., only β-anomer was obtained for the protected Hp-s1 12, but the yield was poor, only 25%. On the other hand, if compound 9 was first treated with $Cu(OAc)_2$ in MeOH at −10° C. to selectively remove the picoloyl group and then protected phytoceramide 11 was glycosylated with the resulting disaccharide 10, the yield increased to 93% under the same conditions as those described for disaccharide 9. The yield of Hp-s1 analogue 13 was also high (87%) with excellent stereoselectivity (β only). The protected Hp-s1 analogues 12 and 13 were then deprotected to produce the desired ganglioside Hp-s1 respectively in the yield of 75% and 89%.

Scheme I.
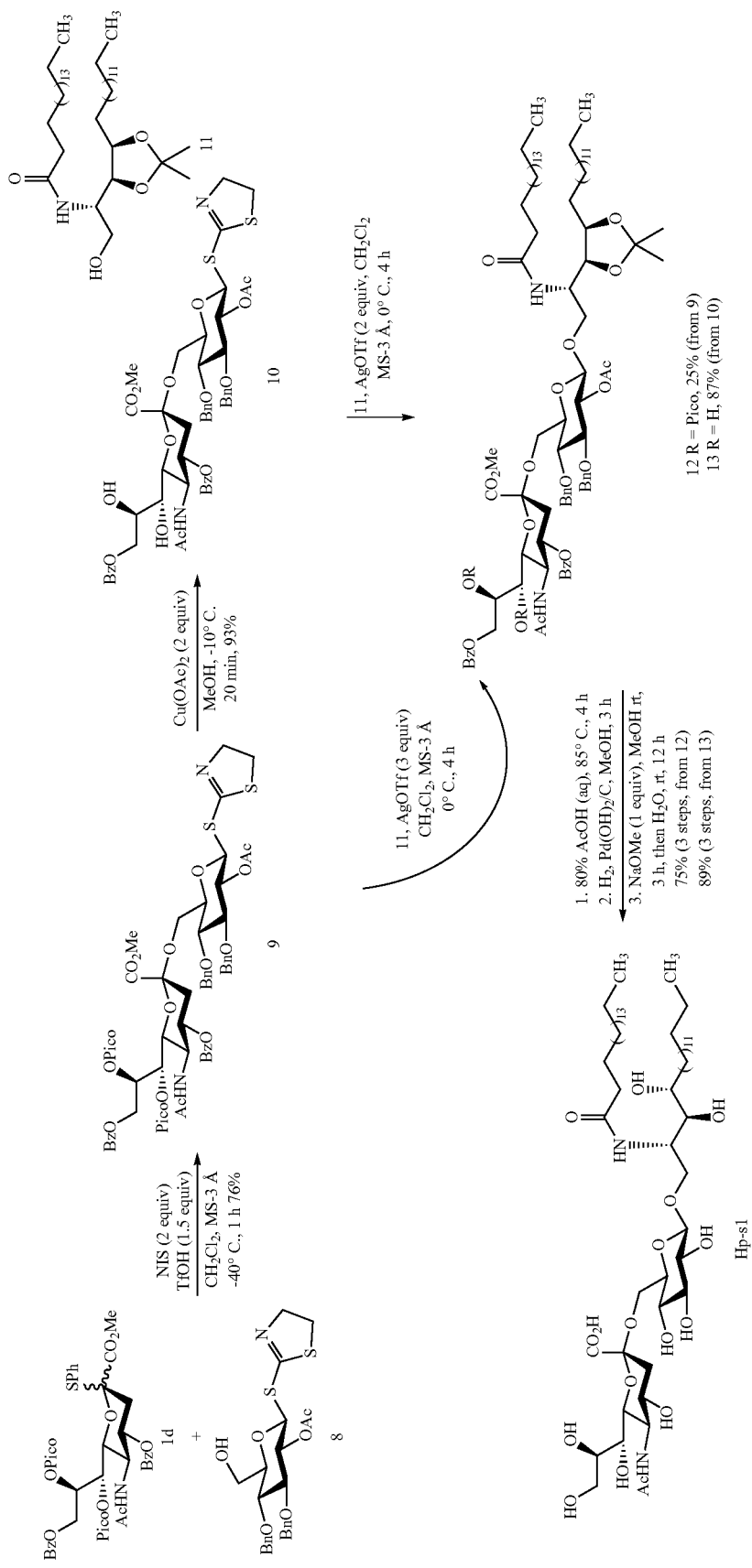

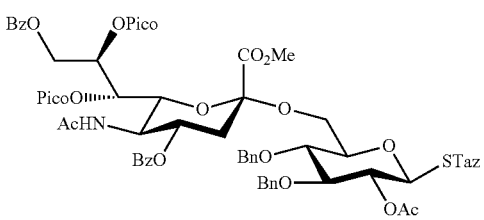
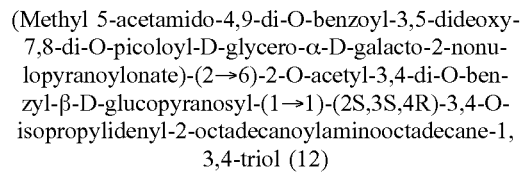

2-Thiazolinyl (methyl 5-acetamido-4,9-di-O-benzoyl-3,5-dideoxy-7,8-di-O-picoloyl-D-glycero-α-D-galacto-2-nonulopyranoylonate)-(2→6)-2-O-acetyl-3,4-di-O-benzyl-β-D-glucopyranoside (9)

Treatment of thiosialoside 1d (0.500 g, 0.60 mmol), glucopyranoside acceptor 8 (0.360 g, 0.72 mmol) and activated 3 Å powdered molecular sieves (0.600 g) with $CH_2Cl_2$ (12 mL) in the presence of NIS (0.271 g, 1.20 mmol) and TfOH (0.080 mL, 0.90 mmol) was according to the general procedure in 1 h. The produced yellowish syrup residue were purified by flash column chromatography on silica gel using ethyl acetate then acetone/$CH_2Cl_2$ (1/1, v/v) as the eluent to give to produce 0.560 g of colorless syrup disaccharide 9 in 76% yield: $R_f$=0.43 (acetone:$CH_2Cl_2$=1:1 (v/v)); $[α]^{30}_D$ +72.1 (c 0.13, $CHCl_3$); FT-IR (neat) $ν_{max}$ 3318, 2922, 2854, 1736, 1674, 1576, 1445, 1370, 1280, 1237, 1122, 1078, 753, 710, 612 cm$^{-1}$; $^1$H NMR (400 MHz, $CDCl_3$) δ 8.74 (d, J=4.4 Hz, 1H), 8.67 (d, J=4.4 Hz, 1H), 8.07 (d, J=7.8 Hz, 1H), 7.99-7.92 (m, 5H), 7.80 (td, J=7.7, 1.4 Hz, 1H), 7.62 (td, J=7.7, 1.6 Hz, 1H), 7.53-7.46 (m, 3H), 7.41-7.20 (m, 16H), 6.05-6.04 (m, 2H), 5.72 (d, J=9.6 Hz, 1H), 5.27 (d, J=10.4 Hz, 1H), 5.14 (ddd, J=12.7, 8.8, 4.6 Hz, 1H), 5.08 (dd, J=10.4, 9.2 Hz, 1H), 4.97-4.29 (m, 9H), 4.27-4.09 (m, 2H), 3.83-3.69 (m, 3H), 3.60 (dd, J=9.6, 2.2 Hz, 1H), 3.49 (s, 3H), 3.32 (t, J=8.1 Hz, 2H), 2.87 (dd, J=12.7, 4.6 Hz, 1H), 2.09 (t, J=12.7 Hz, 1H), 1.95 (s, 3H), 1.79 (s, 3H); $^{13}$C NMR (100 MHz, $CDCl_3$) δ 170.4 (C), 169.5 (C), 167.6 (C), 166.1 (C), 165.8 (C), 163.8 (C), 163.7 (C), 163.5 (C), 149.9 (CH), 149.5 (CH), 147.7 (C), 147.1 (C), 138.0 (C), 138.0 (C), 137.0 (CH), 136.9 (CH), 133.2 (CH), 132.8 (CH), 129.6 (CH), 129.6 (C), 129.3 (C), 128.3 (CH), 128.3 (CH), 128.2 (CH), 127.9 (CH), 127.7 (CH), 127.6 (CH), 126.9 (CH), 126.9 (CH), 125.5 (CH), 125.4 (CH), 99.1 (C), 84.0 (CH), 83.1 (CH), 78.4 (CH), 77.0 (CH), 75.1 ($CH_2$), 74.8 ($CH_2$), 72.7 (CH), 71.2 (CH), 70.5 (CH), 70.1 (CH), 69.1 (CH), 64.0 ($CH_2$), 63.4 ($CH_2$), 62.8 ($CH_2$), 52.5 ($CH_3$), 49.3 (CH), 41.8 ($CH_2$), 38.1 ($CH_2$), 34.9 ($CH_2$), 26.9 ($CH_2$), 24.8 ($CH_2$), 23.0 ($CH_3$), 20.8 ($CH_3$); HRMS-ESI [M+Na]$^+$ Calcd for $C_{63}H_{62}N_4O_{18}S_2Na$ 1249.3394, Found 1249.3369.

(Methyl 5-acetamido-4,9-di-O-benzoyl-3,5-dideoxy-7,8-di-O-picoloyl-D-glycero-α-D-galacto-2-nonulopyranoylonate)-(2→6)-2-O-acetyl-3,4-di-O-benzyl-β-D-glucopyranosyl-(1→1)-(2S,3S,4R)-3,4-O-isopropylidenyl-2-octadecanoylaminooctadecane-1,3,4-triol (12)

A mixture of the sialyl donor 9 (0.110 g, 0.09 mmol), and acceptor 11 (0.067 g, 0.11 mmol), and activated 3 Å powdered molecular sieves (0.124 g) in anhydrous $CH_2Cl_2$ (0.9 mL) was stirred at room temperature for 1 h under nitrogen to remove any trace amounts of water. The reaction mixture was then cooled to 0° C. followed by addition of AgOTf (0.500 g, 0.27 mmol). Continuously stirred at this temperature until TLC showed the reaction to be complete, the reaction mixture was carefully quenched with triethylamine and then filtered through a short pad of Celite. The filtrate was washed with cold saturated aqueous $Na_2S_2O_3$, and brine, dried over $MgSO_4$, filtered, and concentrated in vacuo. The produced yellowish syrup residue were purified by flash column chromatography on silica gel using acetone and $CH_2Cl_2$ (1/2, v/v) as the eluent to give to produce 0.038 g of colorless syrup disaccharide 12 in 25% yield: $R_f$=0.30 (ethyl acetate); $[α]^{30}_D$ +45.5 (c 0.21, $CHCl_3$); FT-IR (neat) $ν_{max}$ 3306, 3065, 2925, 2855, 1736, 1670, 1544, 1458, 1371, 1279, 1120, 753, 709, 614 cm$^{-1}$; $^1$H NMR (400 MHz, $CDCl_3$) δ 8.75 (d, J=4.0 Hz, 1H), 8.67 (d, J=4.0 Hz, 1H), 8.07 (d, J=7.8 Hz, 1H), 7.98-7.91 (m, 5H), 7.80 (td, J=7.8, 1.7 Hz, 1H), 7.63 (td, J=7.8, 1.7 Hz, 1H), 7.53-7.47 (m, 3H), 7.42-7.19 (m, 15H), 6.10-6.03 (m, 2H), 5.85 (d, J=8.2 Hz, 1H), 5.70 (d, J=9.6 Hz, 1H), 5.15-5.09 (m, 1H), 4.97-4.62 (m, 6H), 4.50 (dd, J=10.9, 1.4 Hz, 1H), 4.36-4.28 (m, 4H), 4.12-4.03 (m, 3H), 3.96 (dd, J=10.0, 3.6 Hz, 1H), 3.77-3.72 (m, 2H), 3.64 (t, J=9.1 Hz, 1H), 3.57 (dd, J=10.0, 1.8 Hz, 1H), 3.49 (s, 3H), 2.84 (dd, J=12.7, 4.4 Hz, 1H), 2.14-2.11 (m, 3H), 1.95 (s, 3H), 1.80 (s, 3H), 1.58-1.47 (m, 4H), 1.35 (s, 3H), 1.25 (s, 55H), 0.88 (t, J=6.8 Hz, 6H); $^{13}$C NMR (100 MHz, $CDCl_3$) δ 172.7 (C), 170.3 (C), 169.8 (C), 167.9 (C), 166.5 (C), 166.1 (C), 164.1 (C), 164.0 (C), 150.2 (CH), 149.8 (CH), 148.1 (C), 148.1 (C), 147.4 (C), 138.4 (C), 138.2 (C), 137.1 (CH), 137.0 (CH), 133.5 (CH), 133.1 (CH), 130.0 (CH), 129.9 (CH), 129.8 (C), 129.4 (C), 128.6 (CH), 128.6 (CH), 128.5 (CH), 128.4 (CH), 128.2 (CH), 128.0 (CH), 127.9 (CH), 127.8 (CH), 127.1 (CH), 127.0 (CH), 125.8 (CH), 125.6 (CH), 107.9 (C), 101.3 (CH), 99.3 (C), 82.9 (CH), 77.9 (CH), 77.6 (CH), 76.3 (CH), 75.2 ($CH_2$), 75.0 ($CH_2$), 74.3 (CH), 73.5 (CH), 72.7 (CH), 69.9 (CH), 69.8 (CH), 69.2 ($CH_2$), 69.1 (CH), 63.7 ($CH_2$), 63.0 ($CH_2$), 52.7 ($CH_3$), 50.0 (CH), 48.2 (CH), 38.5 ($CH_2$), 36.9 ($CH_2$), 32.1 ($CH_2$), 29.9 ($CH_2$), 29.8 ($CH_2$), 29.8 ($CH_2$), 29.7 ($CH_2$), 29.7 ($CH_2$), 29.6 ($CH_2$), 29.6 ($CH_2$), 29.5 ($CH_2$), 29.2 ($CH_2$), 28.1 ($CH_3$), 26.7 ($CH_2$), 25.8 ($CH_3$), 25.8 ($CH_2$), 23.3 ($CH_3$), 22.8 ($CH_2$), 21.2 ($CH_3$), 14.3 ($CH_3$); HRMS-ESI [M+Na]$^+$ Calcd for $C_{99}H_{134}N_4O_{22}Na$ 1753.9382, Found 1753.9383.

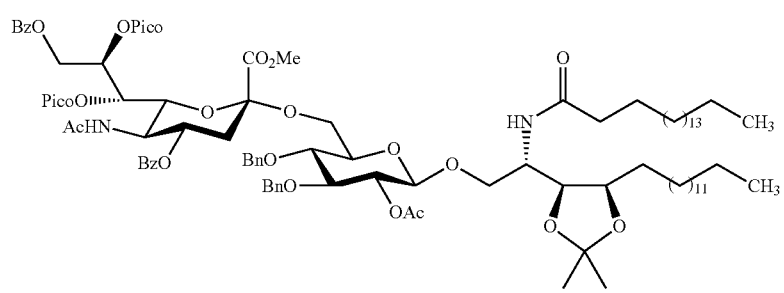

12

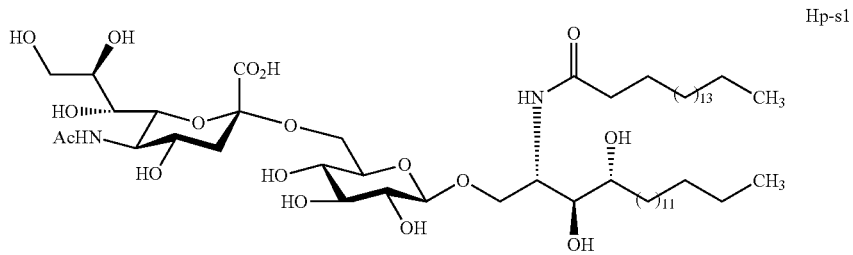

Hp-s1

Synthesis of Target Compound Hp-s1

The isopropylidene acetal 12 (0.050 g, 28.90 μmol) was dissolved in a solution of 80% aqueous AcOH (10 mL) at 0° C. and then the mixture was continuously stirred for 4 h at 85° C. The reaction mixture was co-evaporated with toluene. The resulting colorless syrup diol, without further purification, was dissolved in MeOH (10 mL) and added 20% Pd(OH)$_2$/C (0.003 g) at room temperature. The reaction mixture was stirred under hydrogen (50 psi) at room temperature for 1 h. The Pd(OH)$_2$/C was removed through a short pad of SiO$_2$/Celite and the filter was washed with MeOH. The filtrate was concentrated in vacuo. The resulting colorless syrup tetraol, without further purification, was dissolved in dry MeOH (0.27 mL) and then MeONa (1 mg, 0.027 mmol) was added to this solution at 0° C. After stirring for 3 h at room temp, H$_2$O (0.15 mL) was added to the reaction mixture. After completing the soapnification, the solution was neutralized with Dowex 50w×8 [H$^+$]. The resin was filtered out and washed with MeOH/CH$_2$Cl$_2$ (3:1, v/v). The filtrate was concentrated under reduced pressure to give a white solid residue. After recrystallization (MeOH/CH$_2$Cl$_2$/EtOAc) of the afforded 22 mg of Hp-s1 as a white solid compound in 75% yield over three steps: $R_f$=0.23 (MeOH:CH$_2$Cl$_2$=1:1 (v/v)); $[\alpha]^{24}_D$ −1.3 (c 0.20, MeOH:CHCl$_3$=3:1); FT-IR (neat) $v_{max}$ 3373, 2921, 2853, 1639, 1552, 1481, 1372, 1314, 1204, 1116, 1080, 1040, 760 cm$^{-1}$; $^1$H NMR (400 MHz, CD$_3$OD:CDCl$_3$=3:1) δ 4.26 (d, J=7.7 Hz, 1H), 4.17-4.05 (m, 3H), 3.86-3.82 (m, 2H), 3.77-3.61 (m, 6H), 3.59-3.51 (m, 3H), 3.45-3.32 (m, 3H), 3.21 (t, J=8.4 Hz, 1H), 2.74 (dd, J=12.3, 4.2 Hz, 1H), 2.21 (t, J=7.4 Hz, 2H), 2.01 (s, 3H), 1.76 (t, J=12.3 Hz, 1H), 1.61-1.39 (m, 4H), 1.28 (s, 52H), 0.89 (t, J=6.8 Hz, 6H); $^{13}$C NMR (100 MHz, CD$_3$OD:CDCl$_3$=3:1) δ 174.6 (C), 174.2 (C), 170.5 (C), 103.4 (CH), 98.2 (C), 76.1 (CH), 74.9 (CH), 73.6 (CH), 73.5 (CH), 73.4 (CH), 71.8 (CH), 71.1 (CH), 69.3 (CH), 69.1 (CH$_2$), 68.7 (CH), 67.3 (CH), 63.2 (CH$_2$), 62.3 (CH$_2$), 52.5 (CH), 50.4 (CH), 40.2 (CH$_2$), 36.2 (CH$_2$), 31.8 (CH$_2$), 31.8 (CH$_2$), 31.1 (CH$_2$), 29.7 (CH$_2$), 29.6 (CH$_2$), 29.6 (CH$_2$), 29.6 (CH$_2$), 29.6 (CH$_2$), 29.6 (CH$_2$), 29.5 (CH$_2$), 29.5 (CH$_2$), 29.4 (CH$_2$), 29.4 (CH$_2$), 29.2 (CH$_2$), 29.2 (CH$_2$), 25.9 (CH$_2$), 25.8 (CH$_2$), 22.5 (CH$_2$), 21.8 (CH$_3$), 13.6 (CH$_3$); HRMS-ESI [M-H]$^-$ Calcd for C$_{53}$H$_{99}$N$_2$O$_{17}$ 1035.6949, Found 1035.6939.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A sialyl donor of formula (I) for the synthesis of gangliosides,

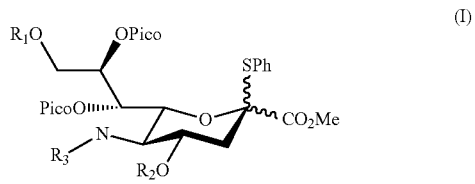

(I)

wherein,

R$_1$ and R$_2$ are independently benzoyl, toluenesulfonyl, pivaloyl or acetyl optionally substituted with a halogen; and R$_3$ is acetyl or —(O)CCH$_2$OH.

2. The sialyl donor of claim 1, wherein the sialyl donor of formula (I) is any of the followings, Compound 1d

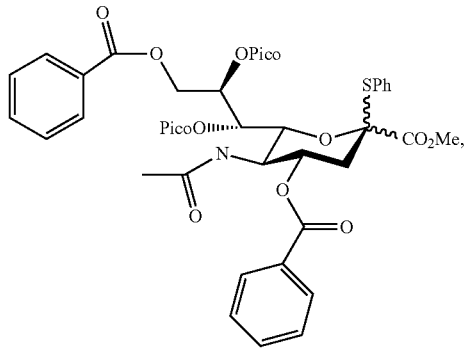

compound 1d-2

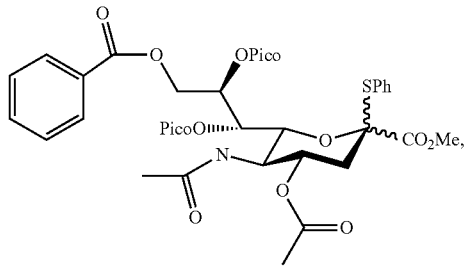

compound 1d-3
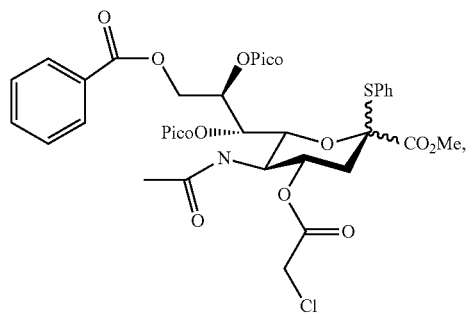
Compound 1d-4
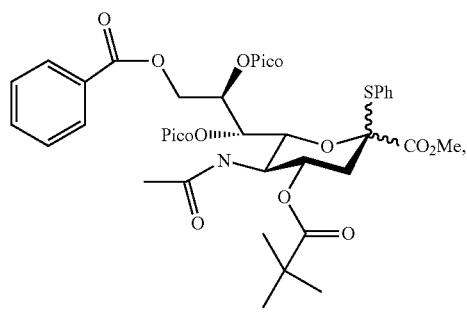
compound 1d-5
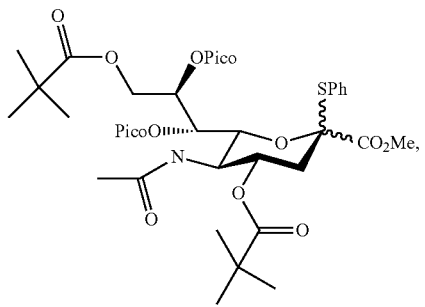
compound 1d-6
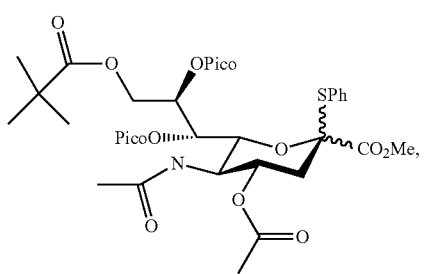
Compound 1d-7
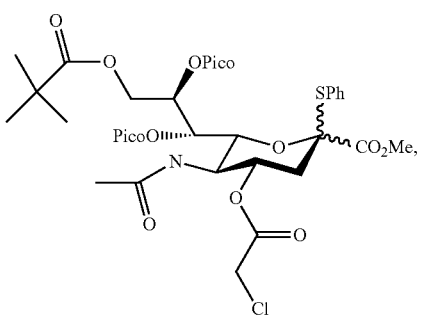
compound 1d-8
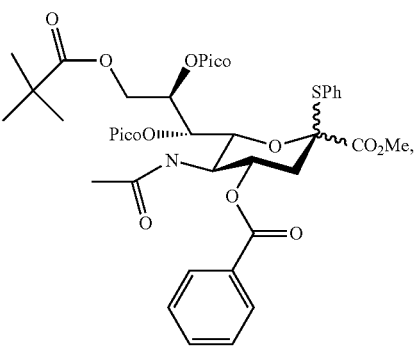
compound 1d-9
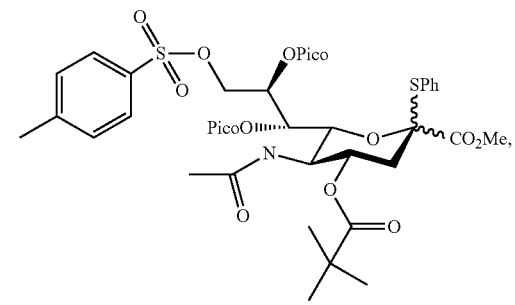
Compound 1d-10
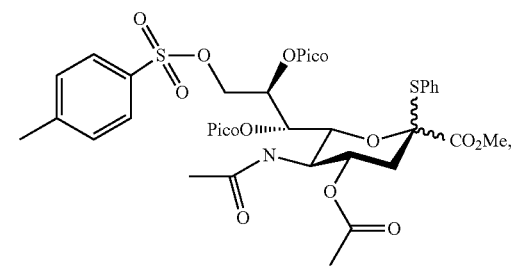
compound 1d-11
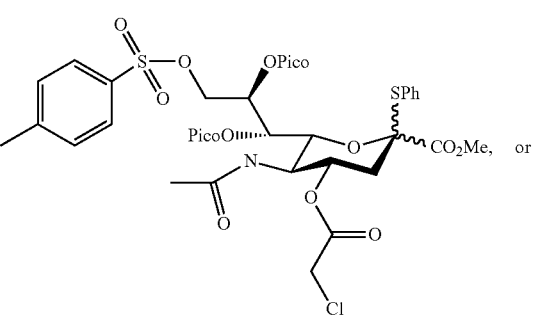
or compound 1d-12

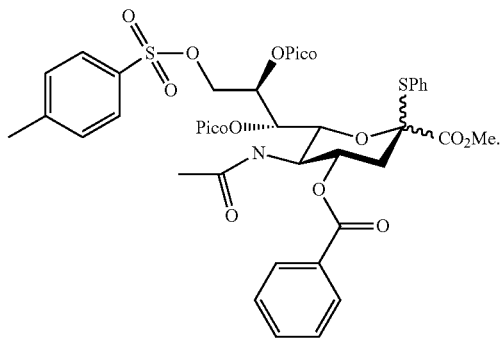

3. The sialyl donor of claim 1, wherein in the sialyl donor of formula (I), $R_1$ and $R_2$ are independently benzoyl, and $R_3$ is acetyl.

4. A method for synthesizing a sialoside comprising:
(a) coupling a sialyl donor with a glycosyl acceptor having a primary hydroxyl group in the presence of N-iodosuccinimide (NIS) and trifluoromethanesulfonic acid (TfOH) under suitable conditions; and
(b) isolating the sialoside, which has an α-glycosidic linkage;

wherein, the silalyl donor has the structure of formula (I):

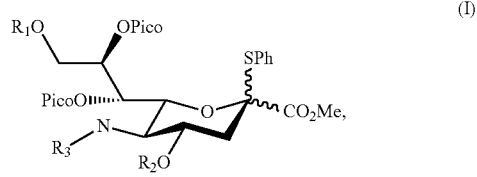

(I)

in which $R_1$ and $R_2$ are independently benzoyl, toluenesulfonyl, pivaloyl or acetyl optionally substituted with a halogen; and $R_3$ is acetyl or —(O)CCH$_2$OH.

5. The method of claim 4, wherein in the step (a), the coupling is performed in a solvent selected from the group consisting of, $CH_3CN$, $CH_3Cl$, and $CH_2Cl_2$ at a temperature between −20° C. to −60° C.

6. The method of claim 5, wherein in the step (a), the coupling is performed in $CH_2Cl_2$ at the temperature of −40° C.

7. The method of claim 4, wherein in the step (a), the coupling reaction is conducted in the presence of a powdered molecular sieve.

8. The method of claim 4, wherein the sialyl donor of formula (I) is any of the followings, Compound 1d

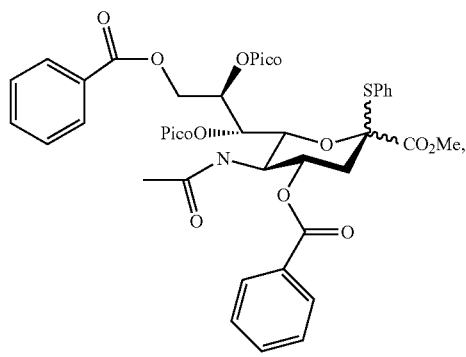

compound 1d-2 compound 1d-3

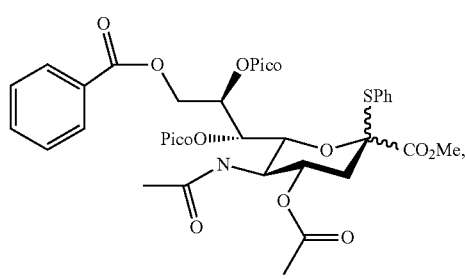

Compound 1d-4

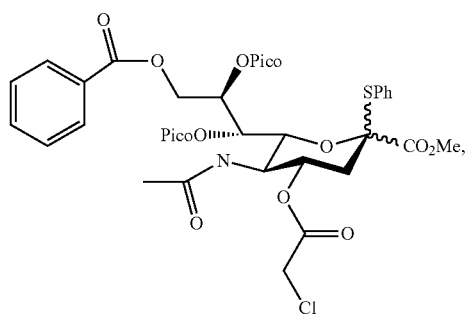

compound 1d-5

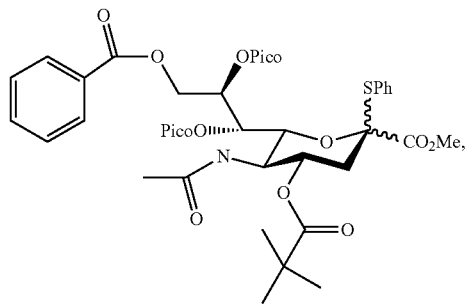

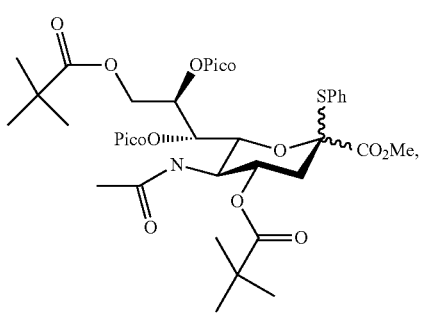

compound 1d-6
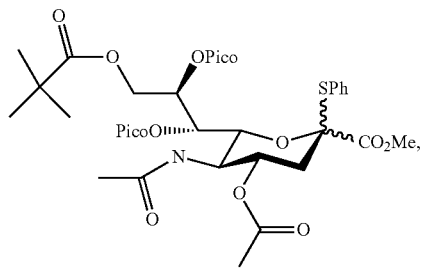
Compound 1d-7
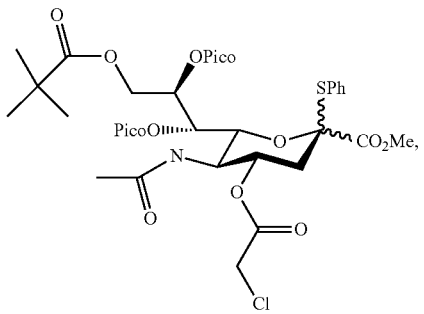
compound 1d-8
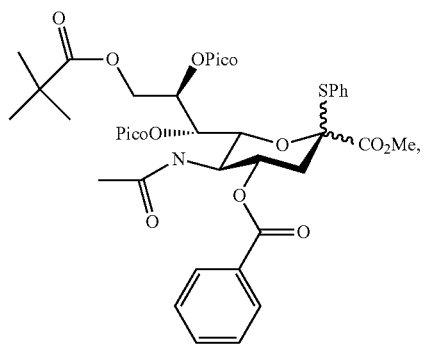
compound 1d-9
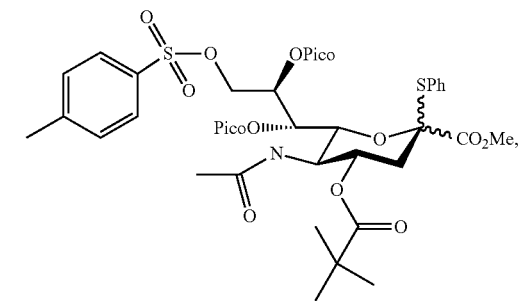
Compound 1d-10
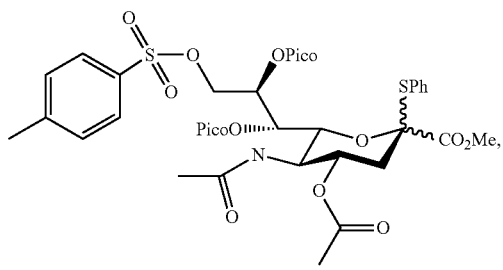
compound 1d-11
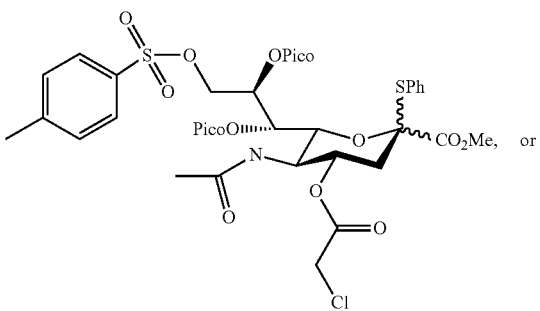
or
compound 1d-12
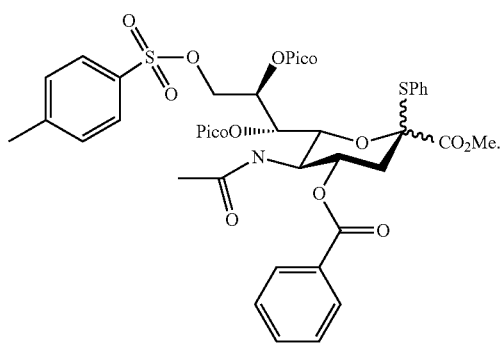
9. The method of claim 4, wherein in the sialyl donor of formula (I), $R_1$ and $R_2$ are independently benzoyl, and $R_3$ is acetyl.
* * * * *